US010893822B2

(12) United States Patent
Hendler et al.

(10) Patent No.: US 10,893,822 B2
(45) Date of Patent: Jan. 19, 2021

(54) METHOD AND SYSTEM FOR USE IN MONITORING NEURAL ACTIVITY IN A SUBJECT'S BRAIN

(75) Inventors: Talma Hendler, Tel-Aviv (IL); Nathan Intrator, Tel-Aviv (IL); Ilana Klovatch, Petach-Tikva (IL); Sivan Kinreih, Ramat-Efal (IL); Yehudit Meir-Hasson, Rehovot (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 293 days.

(21) Appl. No.: 13/983,419

(22) PCT Filed: Feb. 2, 2012

(86) PCT No.: PCT/IL2012/050036
§ 371 (c)(1),
(2), (4) Date: Jan. 16, 2014

(87) PCT Pub. No.: WO2012/104853
PCT Pub. Date: Aug. 9, 2012

(65) Prior Publication Data
US 2014/0148657 A1 May 29, 2014

Related U.S. Application Data

(60) Provisional application No. 61/438,996, filed on Feb. 3, 2011.

(51) Int. Cl.
*A61B 5/0482* (2006.01)
*A61B 5/055* (2006.01)
(Continued)

(52) U.S. Cl.
CPC .......... *A61B 5/0482* (2013.01); *A61B 5/0042* (2013.01); *A61B 5/0095* (2013.01);
(Continued)

(58) Field of Classification Search
CPC ... A61B 5/0042; A61B 5/0482; A61B 5/0095; A61B 5/0261; A61B 5/04008;
(Continued)

(56) References Cited

U.S. PATENT DOCUMENTS 7,865,235 B2    1/2011  Le et al.
2008/0249430 A1*  10/2008  John .................... A61B 5/0476
                                                         600/544

(Continued)

FOREIGN PATENT DOCUMENTS

WO    2009063463 A2    5/2009
WO    2010127044 A1    11/2010

OTHER PUBLICATIONS

Ben-Simon E, Podlipsky I, Arieli A, Zhdanov A, Hendler T, Never resting brain: Simultaneous representation of two alpha related processes in humans. PLoS ONE; 3(12), 2008.
(Continued)

*Primary Examiner* — Lynsey C Eiseman
*Assistant Examiner* — Amanda L Steinberg

(57) ABSTRACT

A system and method are presented for use in monitoring brain activity of a subject. The system comprises a control unit which comprises: a data input utility for receiving measured data comprising data corresponding to signals measured during a certain time period and being indicative of a subject's brain activity originated from locations in the subject's brain during said certain time period, and a processor utility which is configured and operable for processing the measured data and generating data indicative thereof in the form of a multi-parameter function presenting a relation between frequency and time data of the measured signals and for analyzing said relation and identifying a subject-related signature corresponding to the subject's brain neural activity.

55 Claims, 7 Drawing Sheets

(51) Int. Cl.
    *A61B 5/0476*   (2006.01)
    *A61B 5/00*   (2006.01)
    *A61B 5/026*   (2006.01)
    *A61B 5/04*   (2006.01)
    *A61B 5/0478*   (2006.01)
    *A61B 6/03*   (2006.01)
    *A61B 6/00*   (2006.01)
    *A61B 8/08*   (2006.01)
    *G01R 33/46*   (2006.01)
    *G01R 33/48*   (2006.01)

(52) U.S. Cl.
    CPC ........ *A61B 5/0261* (2013.01); *A61B 5/04008* (2013.01); *A61B 5/04012* (2013.01); *A61B 5/0476* (2013.01); *A61B 5/0478* (2013.01); *A61B 5/055* (2013.01); *A61B 6/032* (2013.01); *A61B 6/037* (2013.01); *A61B 6/501* (2013.01); *A61B 8/0808* (2013.01); *G01R 33/46* (2013.01); *G01R 33/4806* (2013.01)

(58) Field of Classification Search
    CPC . A61B 5/04012; A61B 5/0476; A61B 5/0478; A61B 5/055; A61B 6/032; A61B 6/037; A61B 6/501; G01R 33/4806; G01R 33/46
    See application file for complete search history.

(56) References Cited

U.S. PATENT DOCUMENTS

| | | | |
|---|---|---|---|
| 2009/0030303 A1* | 1/2009 | Pradeep | G06Q 30/00 600/411 |
| 2009/0069707 A1 | 3/2009 | Sandford | |
| 2009/0292180 A1* | 11/2009 | Mirow | G06F 19/363 600/301 |
| 2009/0297000 A1* | 12/2009 | Shahaf | G06K 9/00543 382/128 |
| 2010/0016752 A1 | 1/2010 | Sieracki | |
| 2010/0145215 A1* | 6/2010 | Pradeep | A61B 5/0484 600/544 |
| 2011/0028827 A1 | 2/2011 | Sitaram et al. | |

OTHER PUBLICATIONS

Sadeh B, Zhdanov A, Podlipsky I, Hendler T, Yovel G, The validity of the face-selective ERP N170 component during simultaneous recording with functional MRI, NeuroImage; 42(2):778-786, 2008.

Zhdanov A, Hendler T, Ungerleider L, Intrator N, Inferring functional brain states using temporal evolution of regularized classifiers, Computational Intelligence and Neuroscience; 2007:52609, 2007.

PCTfl120121050036 "International Search Report", dated Sep. 24, 2012.

International Preliminary Report on Patentability dated Aug. 15, 2013 From the International Bureau of WIPO Re. Application No. PCT/IL2012/050036. (19 Pages).

Office Action dated Sep. 8, 2016 From the Israel Patent Office Re. Application No. 227589. (3 Pages).

Office Action dated Oct. 31, 2018 From the Israel Patent Office Re. Application No. 227589 and Its Translation Into English. (11 Pages).

Mantini et al. "Electrophysiological Signatures of Resting State Networks in the Human Brain", Proceedings of the National Academy of Sciences, 104(32): 13150-13175, Aug. 7, 2007.

Gerin et al. "Real-Time fMRI Neurofeedback With War Veterans With Chronic PTSD: A Feasibility Study", Frontiers in Psychiatry, 7(Art.111): 1-11 , Published Online Jun. 21, 2016.

Gruzelier "EEG-Neurofeedback for Optimising Performance. III: A Review of Methodological and Theoretical Considerations", Neuroscience and Biohehavioral Reviews, 44: 159-182, Available Online Mar. 29, 2014.

Summons to Attend Oral Proceedings Pursuant to Rule 115(1) EPC Dated Nov. 4, 2020 From the European Patent Office Re. Application No. 12741756.6. (7 pages).

* cited by examiner

METHOD AND SYSTEM FOR USE IN MONITORING NEURAL ACTIVITY IN A SUBJECT'S BRAIN

FIELD OF THE INVENTION

This invention relates to medical techniques for detecting neural activity in a living brain, and more specifically for analyzing neural activity.

BACKGROUND OF THE INVENTION

In neuroscience, different practices have been developed for detecting neural activity in a living brain. One such practice is electroencephalography (EEG), which measures electrical signals generated by the brain's neurons, via a multitude of electrodes placed on a subject's scalp. The neural signals are transmitted by wires to an EEG monitoring system that records the neural signals, and generates data about the signal variation in time which can be further analyzed and possibly also displayed. EEG enables high temporal resolution, in the order of milliseconds, and is therefore useful for detecting quick changes in the electrical activity of the brain. EEG, however, has undesirably low spatial resolution, i.e. it lacks accuracy for determining with satisfactory resolution the region from which the neural signals are generated.

Another practice relates to spatial scanning (such as fMRI), i.e. scanning a living brain in order to obtain an image of the brain, in which neurally active regions are differentiated from neurally inactive regions. Spatial scanning is known to provide high-resolution spatial data and is used to pinpoint (within a few millimeters) the neurally active areas.

The high spatial resolution (in the order of millimeters) of the fMRI allows delineating functional brain areas. However, fMRI's temporal resolution is too poor to track neural dynamics. The EEG methodology, which has very poor spatial resolution (in the order of centimeters at best), has nonetheless optimal temporal resolution (in the order of milliseconds) that allows the characterization of specific dynamics of neural activity at millisecond time scales. Simultaneous EEG/fMRI recording has been successfully implemented, to combine high spatial resolution of fMRI and high temporal resolution of EEG. The inventors have demonstrated a good signal-to-noise ratio of EEG data co-recorded with fMRI by high correlations ($r>0.9$) between EEG data recorded within and without fMRI, as described for example in Ben-Simon E, Podlipsky I, Arieli A, Zhdanov A, Hendler T, Never resting brain: simultaneous representation of two alpha related processes in humans. PLoS ONE, 2008; 3(12) or in Sadeh B, Zhdanov A, Podlipsky I, Hendler T, Yovel G, The validity of the face-selective ERP N170 component during simultaneous recording with functional MRI, NeuroImage, 2008; 42(2):778-786.

The combined EEG/fMRI-Neuro Feedback (NF) therefore may increase the efficiency of EEG-NF or fMRI-NF with high spatial and temporal resolution that could not be revealed otherwise. In this connection, it should be noted that Neurofeedback is generally a type of biofeedback that uses realtime displays of EEG to illustrate brain activity, often with a goal of controlling central nervous system activity.

The relation between EEG data and spatial scan data (generated for e.g. by fMRI) typically relies on statistics provided via simultaneous EEG and spatial scans (e.g. EEG/fMRI) over multiple subjects and multiple trials on long periods of time, usually using different averaging methods such as correlations, trial averaging etc. For example, the inventors have developed machine learning classification methodology on the interpretation of MEG and EEG activity as described in Zhdanov A, Hendler T, Ungerleider L, Intrator N, Inferring functional brain states using temporal evolution of regularized classifiers, Computational Intelligence and Neuroscience, 2007; 2007:52609. The use of summary statistics extracted from multiple subjects and trials allows for improving the signal-to-noise ratio.

GENERAL DESCRIPTION OF THE INVENTION

There is therefore a need to provide a method and a system for monitoring (e.g. inspection, diagnosing) the subject's brain to create a certain brain activity signature that can be used for various applications, for example for neural feedback.

The technique of the invention is capable of analyzing a relation between temporal and spatial measurements of a subject's brain (e.g. EEG data as temporal data and fMRI as spatial scan data; or solely EEG or the like data obtained from a matrix of electrodes), during the brain activity of the subject. As will be described further below, this is particularly useful to create a neural feedback from the patient's brain, which may then be guided only by using EEG brain activity measurements.

It should be understood that for the purposes of the present invention, the subject can be either in an active state, e.g. performing a certain action, e.g. in response to a certain stimulus, or may be in a passive state, e.g. sleeping. Both such active and passive states will be referred to hereinafter as the "brain state". According to the invention, the measured data is analyzed to create a brain activity signature. The signature may be formed by selected functionally-relevant EEG signals and not by rather arbitrary EEG wave oscillations, such as alpha or theta bands. The choice of relevant EEG signals may be made according to a user's specific correlation between temporal and spatial signals (e.g. EEG signals and spatial scan data). The brain activity signature may be user specific, or may be specific for certain population.

In the description below, the temporal data indicative of a neural signal is referred to as EEG data. However it should be understood that the principles of the invention are not limited to this specific type of data, as well as not limited to electrical-type data, and the term EEG data should therefore be interpreted broadly referring to any suitable known type of temporal data indicative of neural signals. Also, it should be understood that such temporal data is actually indicative of time and frequency parameters, and therefore the term temporal data used hereinbefore should be interpreted as time-frequency data. Such time-frequency data is indicative of the frequency of a signal measured at certain measurement location (on certain electrode) and the time pattern of measurements, e.g. at different measurement locations (on different electrodes) or signal measured at different times on a single electrode.

Further, in the description below, the spatial data is exemplified as measured data of a type different from the temporal data (e.g. fMRI). However, it should be understood that generally, the EEG data collected from a matrix of electrodes may by itself present a certain type of spatial data. Moreover, the time pattern of the collection of electrical signals from the electrodes (i.e. a so-called "dynamic data") may also be used for the analysis.

Generally speaking, the present invention utilizes multiple measurements on the subject's brain to determine a multi-parameter function of the measured signal variation, i.e. a time-frequency function or preferably a spatial-time-frequency function. Generally, such function may be determined from the electrical measurements themselves (using multiple electrodes at different locations with respect to the subject's brain, i.e. different locations of the subject's scalp), or by one or more electrodes for electrical measurements and additional special scan providing image data from different locations in the brain, such as fMRI. Generally, the measurements that are to be performed for the purposes of creating the subject-related brain activity signature may correspond to any known or unknown brain state. In some embodiments, the brain state is taken into consideration, namely the signature is determined per the brain state. The latter may correspond to the brain activity in response to certain one or more stimuli.

The method of analyzing the relation between EEG data and spatial scan data is aimed at determining a relation between the EEG and spatial scan data acquired continuously (during a certain time period) and simultaneously. In this manner, a region of neural activity (provided by the spatial scan data) and an EEG signal originating therefrom can be related to each other, and possibly also to the certain brain condition (such as performance of a certain task; a response to a certain stimulus; or "passive state" (sleeping)). The relation between the EEG data and the spatial data (which may or may not be also related to the brain condition) is expressed in terms of a calculated EEG signature (fingerprint) being a multi-parameter function, i.e. time and frequency measurements from multiple locations within the brain (measured from multiple electrodes). The EEG signature is indicative of neural activity in a subject's brain, which in some applications may correspond to a certain known brain state, e.g. may correspond to a brain response to a certain known stimulus.

According to one broad aspect of the present invention, there is thus provided a method for use in monitoring neural activity of a subject's brain. The method comprises:

providing measured data comprising data corresponding to measured signals originated from locations in the subject's brain during a certain time period and being indicative of a subject's brain activity;

processing the measured data and generating data indicative thereof in the form of a multi-parameter function presenting a relation between frequency and time data of the measured signals;

analyzing said relation and identifying a subject-related signature corresponding to the subject's brain neural activity.

The signature related data can be appropriately recorded to be further used for interpretation of a brain functional state of the subject or for neural feedback. The signature related data includes the subject's signature(s), and may also include data indicative of the subject's brain state(s) corresponding to the signature(s).

In some embodiments, the measured data includes measurement of one or more signals originated in multiple locations in the subject's brain. The multi-parameter function thus corresponds to a relation between time and frequency of the measured signals and multiple locations in the brain from which the measured signals are originated (i.e. is a spatial-time-frequency function). The signature is in the form of a frequency and time function over selected set of locations from the multiple measurement locations.

In some embodiments, such a spatial-time-frequency function can be obtained from the measured data including only measurements of electrical activity along the subject's scalp obtained from a matrix of electrodes at multiple locations (typically, EEG measurements). In some other embodiments, the measured data includes first measured data including measurements of electrical activity obtained from one or more electrodes, i.e. one or more locations on the subject's scalp, and also includes second measured data in the form of spatial scan data from multiple location in the brain obtained for example by fMRI measurements, which associates the electrode location with a corresponding location in the brain from which the signal measured by said electrode is originated. In the latter case, the electrical activity measurements and the spatial scan are carried out simultaneously in order to identify one or more regions of neural activity in the subject's brain and an activity level of the one or more regions corresponding to individual functions of the brain.

According to another broad aspect of the present invention, there is thus provided a method for use in monitoring neural activity of a subject's brain, the method comprising:

providing first measured data in the form of one or more electrical signals measured during a certain time period and being indicative of subject's brain activity collected from one or more measurement locations at the subject's scalp, and second measured data in the form of image data variation within the subject's brain during said certain time period;

processing the first and second measured data and generating a corresponding multi-parameter function presenting a relation between frequency and time data of the one or more measured electrical signals and the multiple measurement locations in the brain;

analyzing said relation and identifying a subject-related signature corresponding to the subject's brain neural activity, the signature being in the form of a frequency and time function over selected set of locations from said multiple measurement locations.

According to yet another broad aspect of the present invention, there is provided a method for use in monitoring neural activity of a subject's brain. The method comprises:

providing measured data comprising data corresponding to signals collected from multiple measurement locations during a certain time period and being indicative of a certain known subject's brain state;

processing the measured data and generating data indicative thereof in the form of a multi-parameter function presenting a relation between frequency and time data of the measured signals and the multiple measurement locations for said known subject's brain state;

analyzing said relation and identifying a subject-related signature corresponding to the subject's brain neural activity at said brain state, the signature being in the form of a frequency and time function over selected set of locations from said multiple measurement locations.

According to yet further broad aspect of the present invention, there is thus provided a method for use in monitoring neural activity of a subject's brain, the method comprising:

providing first measured data in the form of electrical signals measured during a certain time period collected from one or more measurement locations at the subject's scalp and corresponding to a certain known subject's brain state, and providing second measured data in the form of an imaging signal variation within the subject's brain measured during said certain time period;

processing the first and second measured data and generating a corresponding multi-parameter function presenting a relation between frequency and time data of the measured electrical signals and multiple locations in the brain corresponding to the multiple measurement locations;

analyzing said relation and identifying a subject-related signature corresponding to the subject's brain neural activity at said certain brain state, the signature being in the form of a frequency and time function over selected set of locations from said multiple measurement locations, thereby enabling use of the signature for further interpretation of a brain functional state of the subject using the first measured data.

As indicated above, in some embodiments, the first measured data (i.e. time-frequency data) may be acquired by EEG measurements. However, the present invention is not limited to EEG measurements and other temporal measurements such as MEG (Magnetic Encephalography) may be used as well. In this connection, it should also be noted that generally MEG can be used as a spatial scan measurement technique. In this case EEG and MEG may be used for providing temporal data and spatial scan data respectively; or MEG-based time-frequency measurement may be combined with any other spatial scan technique. The EEG measurements and the spatial scan are performed on one or more predetermined regions of the subject's brain. A stimulus (if used) may be applied according to a predetermined procedure operable to activate the one or more predetermined regions of the brain. The spatial scan data can then be used to validate the activation of the one or more regions by the stimulus.

In some embodiments, the method comprises applying different stimuli to the subject in order to stimulate one or more different regions of the subject's brain, performing the EEG measurements and spatial scan for each of the stimuli; and determining and recording, for each of the stimuli, the corresponding one or more EEG signatures.

In some embodiments, the method comprises performing the measurements and analysis on a plurality of subjects and creating a database of EEG signatures, which may or may not include data indicative of the corresponding plurality of the brain state/conditions (e.g., tasks or stimuli).

In some embodiments, the method comprises performing an independent spatial scan inspection of the one or more regions of the subject's brain while under certain brain state, e.g. the application of the certain stimulus, in order to validate a reliability of the EEG signature.

In some embodiments, the method comprises developing a feedback protocol for training a specific subject, e.g. under certain brain activity of the subject, such as application of the certain stimulus, by identifying a modulation of at least one parameter of an EEG signature, while under the application of the certain stimulus, corresponding to a functional state of the subject's brain at which the one or more regions are at a desired activity level, and using the identified signature to select EEG signals indicative of the functional state.

In some embodiments, the method comprises performing an independent non-invasive measurement of at least one physiological property of the subject. The at least one physiological property is of a kind changing in response to neural activity in the one or more regions of the brain.

The spatial scan may be performed by using medical imaging which comprises at least one of the following techniques: a functional magnetic resonance imaging (fMRI) scan; a magnetic resonance imaging (MRI) scan; a magneto encephalographic (MEG) scan; hemoencephalography (HEG); magnetic resonance spectroscopic imaging (MRS); positron emission tomography (PET); photoacoustic imaging; X-ray computed tomography (CT); Single photon emission computed tomography (SPECT); and a scan based on ultrasound tagging of light.

In some embodiments, analyzing the relation between the EEG temporal data and the spatial scan data to identify the EEG signature may comprise optimization of some value of one or more parameters of at least one predetermined model. The optimization of the at least one model may comprise determining a set of EEG measurement locations from which a part of the EEG data is measured corresponding to the one or more regions under certain brain state, e.g. responding to the stimulus by neural activity and determining time points of measurements corresponding to the brain condition, e.g. response to the stimulus.

In some embodiments, the relation between the EEG data and the spatial scan data is analyzed by processing the spatial scan data to classify the corresponding EEG data in accordance with different functional states categories according to the level of neural activation, thereby enabling to distinguish between different functional brain states of the subject using the EEG data.

In some embodiments, the at least one model may comprise a regularized logistic or ridge regression classifier configured to identify frequency bands in the EEG data related to neural activation of the one or more regions. In a specific and non-limiting example, the EEG signature can be developed as a regularized logistic (ridge) regression classifier constructed from instantaneous signal values (i.e. signal amplitude and/or instantaneous signal power) with a model selection and validation to select optimal regularization parameters and to obtain spatial-time-frequency features contributing to the classification. An optimization of value of one or more parameters of at least one predetermined model is provided by analyzing the relation between the EEG data and the spatial scan data. The identification of the EEG signature enables to select and optimize at least one of the following regularization parameters: a position of a least one pair of relevant electrodes on the subject's scalp; and for each pair of electrodes, relevant frequency bands in the EEG data (e.g. for a specific brain state, e.g. response to external stimulus); a frequency of the neural signal (e.g. after the application of the stimulus), a maximal amplitude of the neural signal (e.g. after the application of the stimulus), at least one time point indicative of the best predicted mental state of the brain at which a change in frequency and/or in maximal amplitude is detected (e.g. after the application of the stimulus). The optimization of the model comprises determining a set of EEG measurement locations from which a part of the EEG data is measured corresponding to one or more regions of the brain, e.g. responding to the stimulus by neural activity, and determining selected time points of measurements, e.g. corresponding to the response to the stimulus. The optimization of the at least one model may therefore comprise providing a relation between one or more frequency bands in EEG data taken from one or more electrodes with the spatial scan data to provide inference of the electrodes locations and frequency bands related to neural activation of the one or more regions.

The selection of the above mentioned regularization parameters improves the spatial resolution of EEG as well as the localization of neural activity of interest. By constructing an individualized model analysis comprising model selection and validation, the above mentioned optimal regularization parameters are selected to obtain optimal spatial-time-frequency features. A machine-learning classification methodology based on this model analysis/interpretation is thus provided using EEG data for functional state inference (i.e. up-regulation/down-regulation of limbic regions) enabling an accurate interpretation (brain state) of the EEG activity. The functional state's category is defined according to the level of activation in the spatial scan images. Variations between subjects in the EEG signature are expected and serve as a basis for the modeling of a neural activation index.

In some embodiments, the method comprises predicting the functional state of the subject based on the EEG data. Predicting the functional state of the subject may comprise selecting at least one machine learning/data mining classifier corresponding to the functional state and analyzing the EEG data for validating reliability of the classifier. Predicting the functional state of the subject may also comprise comparing outcome of the classifier for different time points and selecting a time point indicative of the optimal predicted functional state.

The validation of the signature may be performed by analyzing estimated sources of activation using MR-based head models and/or beamformer approach to projection space. Structural or functional information of MRI signals can be used to identify a signature comprising individual volume conductor (head) models that include different conductivities for the skin, skull, and brain compartments (i.e., a so-called boundary-element model). The identification of such type of signature allows then a spatial filtering of the EEG signal for example by using beamformer approach.

According to yet another broad aspect of the present invention, there is also provided a system for use in monitoring brain activity of a subject. The system comprises:
  a control unit comprising:
    a data input utility for receiving measured data comprising data corresponding to signals indicative of a subject's brain activity collected from one or more measurement locations during a certain time period, and
    a processor utility which is configured and operable for processing the measured data and generating data indicative thereof in the form of a multi-parameter function presenting a relation between frequency and time data of the measured signals and for analyzing said relation and identifying a subject-related signature corresponding to the subject's brain neural activity.

According to yet further aspect of the invention, there is provided a system for use in monitoring brain activity of a subject, the system comprising:
  a measurement device configured and operable for measuring signals originating from a subject's brain during a certain time period and generating measured data comprising data corresponding to signals indicative of a subject's brain activity during said certain time period; and
  a control unit connectable to the measurement device for receiving the measured data and comprising a processor utility which is configured and operable for processing the measured data and generating data indicative thereof in the form of a multi-parameter function presenting a relation between frequency and time data of the measured signals and for analyzing said relation and identifying a subject-related signature corresponding to the subject's brain neural activity.

According to yet further aspect of the invention, there is provided a system for use in monitoring brain activity of a subject, the system comprising:
  a measurement device comprising:
    an EEG electrode arrangement configured for placing on a scalp of a subject and detecting electrical signals originated by neural activity of a subject's brain, and for generating EEG data indicative thereof; and
    a spatial scanner configured for scanning the subject's brain and identifying one or more regions of neural activity in the subject's brain and an activity level of the one or more regions corresponding to individual functions of the brain, and generating a spatial scan data; and
  a control unit configured for controlling simultaneous operation of the EEG electrode arrangement and the spatial scanner, the control unit being configured and operable for receiving the EEG data and the spatial scan data, and for determining and analyzing a relation between the EEG data and the spatial scan data to identify an EEG signature indicative of a spatial neural activation of one or more regions in the subject brain, thereby enabling use of the signature for further interpretation of a brain functional state of the subject by using the EEG data.

In some embodiments, the control unit is configured and operable to identify the EEG signature by optimization of value of one or more parameters of at least one predetermined model; the parameters being selected from at least one of: providing a set of EEG measurement locations from which a part of the EEG data is measured corresponding to the one or more regions responding to the stimulus by neural activity; determining time points of measurements corresponding to the response to the stimulus and providing a relation between one or more frequency bands in EEG data with the spatial scan data to obtain inference of the frequency bands related to neural activation of the one or more regions.

In some embodiments, the control unit is configured and operable to identify the signature by determining a classifier corresponding to a functional state and validating the reliability of the logistic regression classifier.

In some embodiments, the system comprises a non-invasive physiological measuring device, for independently measuring at least one physiological property of the subject being of a kind changing in response to neural activity in the one or more regions of the brain. The control unit is further configured for receiving the measured physiological response and ensuring that the signature found reliably indicates neural activity at the corresponding region, via comparison of the measured physiological response to a previously determined physiological response associated with neural activity of the corresponding region. The control unit may also be further configured for receiving the measured physiological response and processing said measured physiological response to improve the identification of the EEG signature.

According to another broad aspect of the present invention, there is also provided a system for creating a database for use in monitoring brain activity of a subject. The system comprises a data input utility for receiving measured data comprising data corresponding to signals indicative of a subject's brain activity collected from multiple measurement locations during a certain time period (e.g. EEG data and spatial scan data simultaneously measured on brain of a specific subject), and a data processor utility configured for processing the measured data and generating data indicative thereof in the form of a multi-parameter function presenting a relation between frequency and time data of the measured signals and the multiple measurement locations (e.g. a relation between the EEG data and the spatial scan data), and for analyzing said relation and identifying a subject-related signature corresponding to the subject's brain neural activity, the signature being in the form of a frequency and time function over selected set of locations from said multiple measurement locations (e.g. one or more EEG signatures indicative of a certain spatial neural activation as corresponding to one or more regions in the subject brain), thereby enabling use of the signature for further interpretation of a brain functional state of subjects by using the measured data (e.g. EEG data).

Once the EEG signature is recorded, it is possible to identify one or more regions of neural activity and/or the level of the neural activity caused by a specific stimulus and therefore to interpret a brain functional state via an EEG measurement and a processing of the EEG data. In this manner, the recording of the signature enables some diagnostic practices which rely on spatial scans, to be performed via EEG alone based on predetermined EEG signature. The EEG signature may be derived from previous simultaneous spatial and EEG scan of the subject or from a database of signatures. By greatly reducing a need for bulky and expensive spatial scanners (such as scanners based on fMRI, Hemoencephalography (HEG), magneto encephalography (MEG), Magnetic resonance spectroscopic imaging (MRS), positron emission tomography (PET), X-ray computed tomography (CT), Single photon emission computed tomography (SPECT), or ultrasound tagging of light), the cost and space required for performing many medical practices is reduced. Furthermore, because an EEG signature of the spatial brain activity is developed, practices aimed at analyzing subject-dependent spatial brain patterns may also be performed with a greatly reduced use of spatial scanners.

For example, EEG-based neurofeedback (EEG-NF) is a practice that may be improved by the determination of the signature. This is because, typically, protocols used in EEG-NF are not specific enough to target a certain brain area and consequently a certain brain function. The signature determined in the present invention allows identification of neurally active regions in the brain and/or identification of stimuli received by the brain, via an analysis of EEG data alone. Therefore, the present invention provides, inter alia, a technique (and a related system) for performing EEG-NF targeted at improving a subject's modulation of one or more determined regions relating to individual functions of the brain. Moreover, by performing EEG-NF using the technique of the present invention, relevant neural network as indicated by the spatial scan may be targeted. The targeting network is expected to vary from subject to subject.

When the technique of the present invention is used with NF applications, an EEG limbic modulation index is developed to correlate between spatial scan-based NF with EEG signal changes. The characteristic EEG index is deduced from the fMRI activation. The index is composed of EEG features characterizing the spatial scan-targeted brain activity during NF.

According to another broad aspect of the present invention, there is also provided a method for use in performing neurofeedback. The method comprises providing a predetermined signature related data (EEG signature related data) comprising a frequency and time function of electrical signal measured from a set of locations in the subject's brain corresponding to a certain brain condition (e.g. in response to stimulus), the predetermined signature being indicative of a spatial neural activation of one or more regions in a subject brain corresponding to individual functions of the brain while under the certain brain condition and thus corresponding to a predicted certain activity state related to a certain brain condition; subjecting the brain to said condition (e.g. by applying the stimulus) to activate the one or more brain regions; performing the electrical measurements on the subject's brain while under the certain brain condition, and generating measured data indicative thereof (e.g. EEG data); processing the measured data using the predetermined signature to identify one or more parameters indicative of neural activation of the one or more regions while under the given brain condition, and selecting from the measured data signals related to the neural activation.

In some embodiments, the method comprises extracting a modulation of limbic activity from the EEG signals, comparing the extracted modulation of limbic activity to a desired modulation of limbic activity corresponding to the predicted certain activity state; and determining a degree of correlation between the modulation of limbic activity and the desired modulation of limbic activity, enabling to determine a psychological evaluation of the subject.

In some embodiments, the method comprises upon identifying that the extracted modulation and the desired modulation have a high degree of correlation, conveying a message indicating success to the subject; and upon identifying that the extracted modulation and the desired modulation have a low degree of correlation, conveying a message indicating failure to the subject, such that the subject is trained to monitor limbic activity modulation of the one or more region.

In some embodiments, the method comprises after conveying a message indicating failure to the subject, repeating the EEG measurement on the subject while under certain brain condition (e.g. the application of the stimulus) and processing the EEG data. Conveying the message may comprise at least one of: conveying a sound to the subject; displaying an image to the subject; and displaying a video to the subject.

In some embodiments, providing the predetermined EEG signature comprises providing an EEG limbic modulation index indicative of the modulation of the limbic activity.

In some embodiments, the method comprises controlling a timing of the EEG measurement period, and a timing of the application of the stimulus to a subject.

In some embodiments, the method comprises simultaneously with performing the EEG scan: measuring a physiological property of the subject; and after extracting the modulation: using a predetermined signature-to-region map to identify the active region in the subject's brain; and validating the determined regions, by comparing the measured physiological property with a predetermined physiological property associated with neural activity in the identified region.

According to another broad aspect of the present invention, there is also provided a system for use in performing neurofeedback. The system comprises a measurement unit (e.g. an EEG measurement unit) configured for detecting electrical signals originated by neural activity of a subject's brain, and generating measured data (e.g. EEG data) indicative thereof; and a control unit comprising: (i) a memory utility for storage of a predetermined signature (e.g. EEG signals) indicative of spatial neural activation of one or more regions in a subject brain corresponding to individual functions of the brain, the signature corresponding to a predicted subject's brain activity while under certain brain condition (e.g. application of a stimulus); and (ii) a data processor configured and operable for receiving the measured data and for processing the measured data utilizing stored data about the predetermined signature to identify one or more parameters corresponding to neural activation of one or more regions under the certain brain condition of a specific subject during the measurements.

In some embodiments, the system comprises an output interface, configured for conveying a subject a feedback message in real time indicating success or failure of the subject to provide a desired response to a given stimulus, according to a signal generated by the control unit such that the subject is trained to regulate the neural activity of the region via the feedback message.

In some embodiments, the control unit is configured and operable for determining modulation indicative of an activity of a region of the subject's brain, selecting from the EEG data spectrum by using the parameters, EEG signals related to the neural activation and extracting a modulation of limbic activity from the EEG data; for comparing the extracted modulation to a desired modulation indicative of a desired activity state of the subject's brain, for determining a psychological evaluation of the subject and generating a feedback signal thereof. The control unit may be configured and operable to identify the predetermined signature by analyzing a relation between the EEG data with the spatial scan data associated with the activation level of localized brain regions. The control unit may be configured for controlling a timing of the EEG measurement period and a timing of the instruction to the subject within the EEG measurement period by using the parameters, the timing being related to the neural activation.

In some embodiments, the output interface comprises at least one of a display and a speaker, and earphones.

In some embodiments, the control unit is configured and operable to select the EEG data generated by the EEG electrode arrangement, EEG data generated by electrodes generating data indicative of neural activation of the one or more regions. The control unit may be configured and operable to process the EEG data and transform the EEG data to an EEG spectral data and to select the EEG spectral data frequency bands indicative of neural activation of one or more regions.

In some embodiments, the system comprises a non-invasive physiological measuring device configured for independently measuring at least one physiological property of the subject being of a kind changing in response to neural activity in the one or more regions of the brain. The control unit is further configured for using the signature to identify the active region or network in the subject's brain, and validating neural activity in the determined regions by comparing the measured physiological property with a predetermined physiological property associated with neural activity in the identified region. The physiological measuring device may comprise at least one of an electrocardiography device and a skin conductance measurement device.

An aspect of some embodiments of the present invention relates to a method and system for identifying a signature in EEG data, the signature being indicative of neural activity including a specific neural active region or network of regions of the brain, and of a brain state/condition causing such neural activity. The determination of the signature enables a construction of a brain map relating at least one specific signature to at least one specific brain condition producing neural activity in at least one specific region/network of the brain. This map may be used for converting data obtained during an EEG-based measurement to spatial and/or functional data, i.e. to accurately pinpoint a region/network from which neural signals detected by means of EEG originate, and a brain condition causing these neural signals. The above-mentioned map may therefore lead to a reduction in the use of typical spatial scans and an increase in the use of EEG scans alone in some applications that require high spatial resolution.

Another aspect of some embodiments of the present invention relates to a technique aimed at greatly reducing the use of spatial scanner such as fMRI scanner in NF practice, and obtaining reliable data indicative of the neural activity of one or more regions/networks in a subject's brain by extracting a signature from EEG data, by reliance on a suitable signature-to-region and/or signature-to-brain state conversion map. This is achieved by extracting from the images of the regional spatial scanning activation, measured in a preliminary EEG/spatial scanner scan, EEG parameters characterizing the spatial scanner-targeted brain activity during NF. As mentioned above, the EEG parameters may include relevant electrodes, time points indicative of the best predicted mental state of the brain and relevant frequency bands in the EEG spectral data for a specific brain state/condition.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
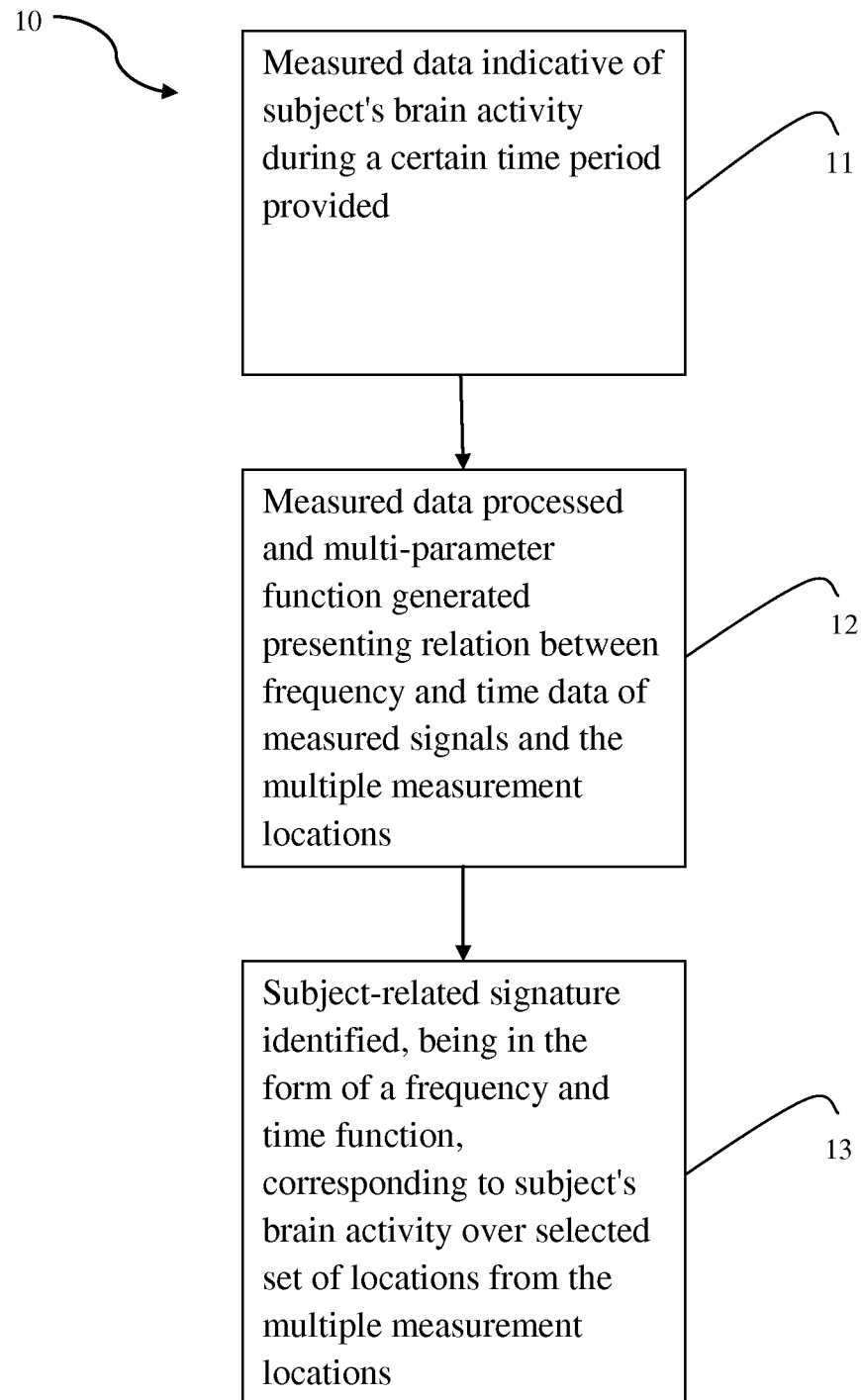
FIG. 1A is a flowchart of a method of the present invention for use in monitoring a subject's brain activity for the purposes of creation a brain activity signature.

Referring to FIG. 1A, there is illustrated a flowchart 10 of a method of the present invention for use in monitoring a subject's brain activity for the purposes of creation a brain activity signature. Measured data is provided (step 11), where the measured data includes data corresponding to signals indicative of a subject's brain activity originated from one or multiple measurement locations in the subject's brain during a certain time period. Such measure data may be provided off-line, i.e. received from a storage device, or may be provided on-line, i.e. directly from and during the actual measurements on a subject. The measured data is processed (step 12) and data indicative thereof is generated in the form of a multi-parameter function presenting a relation between frequency and time data of the measured signals and the multiple measurement locations. The so-obtained relation is analyzed (step 13) analyzed and a subject-related signature corresponding to the subject's brain neural activity is identified, being in the form of a frequency and time function over selected set of locations from said multiple measurement locations.

Figure 1B:
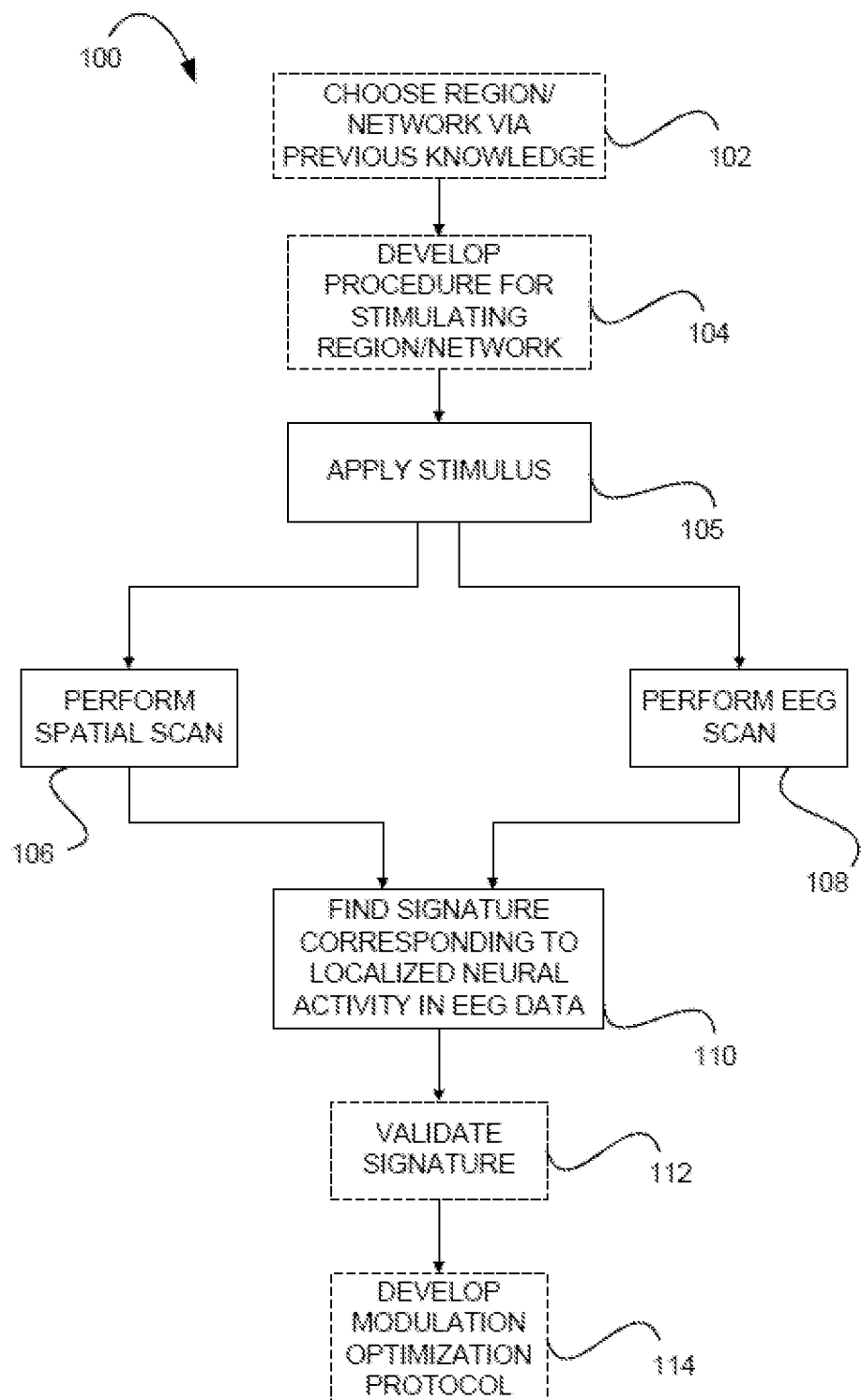
FIG. 1B illustrates a flowchart of a specific example of a method of the present invention for the brain activity signature creation.

FIG. 1B is a flowchart 100 illustrating a specific example of the above-described method for identifying a subject's related signature. In this example, measured data includes electrical measured data such as EEG data. Thus, electrical measured data is provided in the form of electrical signals measured from multiple locations along the subject's scalp (step 102). In this specific not limiting example, the measured data is provided in an on-line mode, namely while performing actual measurements. It should, however, be understood that the present invention of monitoring the subject's brain is not limited to such on-line mode, and can actually be carried out off-line by appropriately processing and analyzing measured data previously collected and stored.

Also, in this specific not-limiting example, the method utilizes measured data corresponding to a given brain condition caused by applying a certain stimulus to a subject at 105. As indicated above, the invention does not necessarily utilize such known brain condition, and not necessarily caused by application of an external stimulus, in order to create the brain activity signature. In this example, EEG measurements of a subject's brain are performed at 108 during a certain time period while under the application of the certain stimulus, and EEG data is generated. Also, in this specific not-limiting example, a separate spatial scan is of the subject's brain is performed at 106 simultaneously with the EEG measurements and second measured data is provided. The measured data (first and second measured data in this specific example) is processed to generate corresponding data in the form of a multi-parameter function presenting a relation between frequency and time data of the measured EEG signals and the multiple measurement locations. Then this function is analyzed to identify a subject-related signature corresponding to the subject's brain neural activity. The signature is in the form of a frequency and time function over selected set of locations from the multiple measurement locations.

More specifically, the measured data is processed and analyzed in order to identify one or more regions of neural activity in the subject's brain and an activity level of the one or more regions corresponding to individual functions of the brain, and generate a spatial scan data corresponding to the EEG data; and analyzing a relation between the EEG data and the spatial scan data, identifying an EEG signature at 110 for the certain brain condition (corresponding to a response of the subject's brain activity to the certain stimulus). The signature can be recorded as being indicative of a spatial neural activation of the one or more regions in the subject brain while under certain brain state/condition, e.g. caused by the certain stimulus, thereby enabling use of the recorded signature for further interpretation of a brain functional state of the subject using EEG data.

In some embodiments of the present invention, one or more regions or a network in the brain is chosen for stimulation at 102, by relying on previous knowledge about the region/network. The region/network may be a location in the brain or a functional organ of the brain. The knowledge may include a function of the region/network, a perceived need for controlling or modulating neural activity in the region/network, and/or an independent validation method for confirming neural activity in the region/network. For example's sake, if the method 100 is performed in order to improve NF, the selected region/network includes a region/network that is associated with a function the modulation of which is desirable. The modulation of limbic activity is known or believed to be controllable via NF. A typical region the modulation of which is improved via NF is the amygdala—a region involved in post-traumatic stress disorder (PTSD). A typical network the modulation of which is improved via NF is, for example, the dorsal anterior cingulated cortex (dACC), which is implicated with enhanced or reduced perception of pain.

It is known that activity of some regions or networks in the brain is associated with measurable physiological effects, such as sweat production or change of heart rate. Detection of such effects provides an independent verification of neural activity of the region/network. Optionally, the region/network chosen for stimulation is selected according to a known physiological effect associated with the region/network activation, in order to increase the reliability of data indicative of neural activity via independent verification.

At 104, a predetermined procedure for stimulating/activating the selected region/network is developed. Such predetermined procedure may include solving a puzzle, watching a movie, hearing a sound. For example, when the method 100 is performed in order to improve an anxiety-decreasing NF technique, the predetermined procedure is aimed at challenging and/or stressing the subject, in order to stimulate a region/network that is particularly active in stress or trauma situations. In such a case, the predetermined procedure may include exposing the subject stress-inducing movies and/or images, or asking the subject to solve unsolvable puzzles, for example.

At 105, one or more external stimuli are applied to the test subject. The stimuli may be applied blindly (i.e. without knowledge of what regions or networks will be activated by the stimuli), or according to the selection of region/network of step 102 and to the predetermined procedure developed at 104.

At 106, a spatial brain scan is made, in order to locate activity in subject's brain before and after the stimulation, to identify which region/network is activated by the stimulation. The spatial scan is performed via one or more medical imaging techniques capable of providing imaging characterized by high spatial resolution, in order to accurately identify the regions where neural activity is increased or decreased as a result of the stimulation.

These techniques may include, for example, magnetic resonance imaging (MRI), functional magnetic resonance imaging (fMRI), Hemoencephalography (HEG), magneto encephalography (MEG), Magnetic resonance spectroscopic imaging (MRS), positron emission tomography (PET), photoacoustic imaging, X-ray computed tomography (CT), Single photon emission computed tomography (SPECT), or ultrasound tagging of light. These techniques may be performed by placing at least one magnetic source and/or electromagnetic source and/or a sensor (infrared) in the vicinity of the scalp to measure the level of neuronal activity in the brain.

Simultaneously with the spatial scan, an EEG recording/measurement is performed at 108, in order to record electrical activity of the brain corresponding to stimulation of the region/network ROI/NOI and to provide an EEG data. This first simultaneous recording of EEG and of a spatial scan determines the first neuroimaging time point. The EEG recording may include bipolar and/or referential measurements, according to the needs/limitations of the user. At this stage, the EEG measurements are taken over a plurality of channels, each channel measuring signals between two electrodes located at different locations on the subject's scalp, on bipolar measurements, or between each channel and a reference channel, in referential measurement. The effect of the stimulus on the measured EEG signal will be stronger in electrodes closer to the activated regions or networks. The spatial scan and EEG recording begin at a predetermined time before the stimulus and end at a predetermined time after the stimulus. In this manner, the change in neural activity in due to the stimulus is detected.

Optionally, an independent non-invasive measurement of a physiological property of the subject being of a type changing in response to neural activity in the desired region/network is performed simultaneously with the spatial brain scan of step 106 and EEG recording of step 108. The measurement of the physiological response is used as a tool to provide an independent verification of the neural activity change in the desired region/network as well as additional data and parameters that may be used for the identification of the EEG signature. For example, if variation of the activity of the desired region/network is known to be associated with a change in sweat production, a measurement of skin conductance (which is indicative of sweat production) may be used in order to verify the neural activity change. If, on the other hand, variation of the activity of the desired region/network is known to be associated with a change in the subject's heart rate, then heart rate is measured (for example by electrocardiography) in order to verify the neural activity change. This verification step may increase accuracy in the interpretation (brain state) of the data acquired in the spatial brain scan of step 106.

Optionally, the measuring/scanning steps 106, 108 are repeated for different stimuli, in order to obtain different pieces of data. Each piece of data pertains to the activation of one of a plurality of regions/networks in the subject's brain. The measurements and analysis may be performed on a plurality of subjects and creating a database of EEG signatures per a plurality of stimuli.

At 110, EEG data obtained as a function of time and of a specific stimulus at 108 is analyzed, in order to identify a signature indicative of neural activity at the region/network as a response to the given stimulus. The signature characterizes a correlation between the EEG signal and the spatial brain activity in response to the stimuli. The signature depends on the region/network of the neural activity and enables to determine a fingerprint of a specific subject for a specific stimulus.

Optionally, in order to extract a reliable signature from the analysis of 110, the analysis is to be based either on repeated measurements (106, 108) performed on a single subject, or on measurements (single or repeated) performed on a plurality of subjects. The choice of whether to use one subject or a plurality of subjects in the method 100 is made according to a user's necessity (such as time constraint, or availability of equipment), and according to a degree of variance in the signature among a plurality of subjects. More specifically, if a signature is observed to reliably indicate neural activity at a specific region/network for one subject but not for other subjects, it may be the case that such signature is an individualized signature for the single subject, and measurements on other subjects may be superfluous. On the other hand, another signature may be observed to vary within an acceptable range for a plurality of subjects, and to be associated with a neural activity of a specific region/network common to the plurality of subjects. In such a case, it may be inferred that this signature is common to many, and measurements performed on a plurality of subjects may increase the reliability of the signature calculation.

The measurements (106, 108) may be performed for a single region/network, or for a plurality of region/network, according to a user's need. If measurements are made relating to activation of different regions/networks for different stimuli, a database may be created, which will enable a comparison between EEG data associated with neural activity in each of a plurality of regions/networks for each stimulus, and the recognition of a plurality of suitable signatures, each signature corresponding to neural activity in a specific region/network for a specific stimulus. When multiple signatures are determined, such that each signature corresponds to neural activity at a specific region/network for a specific stimulus, a three-dimensional brain map may be constructed to relate EEG scan data to spatial and/or functional scan data and stimulus type. The map may be an individual map relating to a single test subject or a common map relating to a plurality of test subjects (and optionally extrapolated to relate the entire species of the test subjects). This map may be useful for performing practices in which the knowledge of the neurally active regions and/or knowledge of the stimuli inducing activation of such regions in the brain is necessary or desirable, while reducing the need for cumbersome and costly spatial scanners. Such a practice is, for example, NF, which is generally performed via EEG measurements or spatial scans. The map may be useful for decreasing of the need for the spatial scan technique, and may enable a user to perform NF with EEG measurements alone (after a preliminary fMRI/EEG session for determining the signatures), using signatures in EEG data to determine which regions or networks are neurally active during the measurement. Alternatively, the map may be used for performing an indirect spatial brain scan via EEG measurements, and replace expensive and cumbersome spatial scanners, at least for some diagnostic techniques.

Optionally, after the signature has been obtained, a validation of the signature is carried out at 112 defining a second neuroimaging time point. The validation includes applying the stimulus of step 105, and repeating an independent spatial scan of 106 simultaneously with the EEG measurement of 108 (and optionally the independent verification), in order to ensure that the signature determined at 110 reliably corresponds to the stimulus and to neural activity at the region/network activated. If the signature extracted from results of the validation measurements is similar to the signature extracted at 110, and corresponds to an activation of the same region or network in the brain, then the signature is deemed reliable.

In the event that the signature is determined for the purpose of performing NF via EEG measurements alone, where each signature in EEG data is used to determine the region/network of neural activity and/or a stimulus causing such activity during the measurement, a protocol for improving brain modulation in NF is developed at 114. The NF procedure is guided by the EEG and is tested against the limbic activation visualized via the spatial scan images. In such a protocol, a set of training repeated sessions is included in a third neuroimaging time point, in order to teach a subject to modulate one or more specific regions/networks of the brain. A modulation of at least one parameter of an EEG signature is identified under the application of the certain stimulus, corresponding to a functional state of the subject's brain at which one or more regions are at a desired activity level. The subjects are trained to regulate the activity of target brain areas via feedback. The modulation is detected by extracting the signatures corresponding to a stimulus and a subsequent activation of the regions/networks, and comparing the extracted signatures to signatures corresponding to a desired modulation (different degree of activity) of the specific regions/networks achieved by a given stimulus. The development of this modulation optimizing protocol includes determining the signatures corresponding to states at which specific regions/networks are at a desired activity state. The identification of the signature enables to select EEG signals indicative of a specific brain functional state. In this manner, a comparison between one or more signatures extracted from the EEG data measured during an NF session and the corresponding signature or signatures corresponding to the desired state of specific region(s)/network(s) will indicate whether the desired modulation has been achieved by the subject, enabling to determine a psychological evaluation.

In a specific and non-limiting example, the experimental data may be acquired as follows: the brain scanning is performed on a 3T (GE, HDXt) MRI scanner with 8-channel head coil. The structural imaging is acquired by a 3D spoiled gradient (SPGR) echo sequence with high-resolution 1-mm slice thickness (FOV: 25*18; matrix: 256*256; TR/TE: 7.3/3.3 ms). Functional imaging (fMRI) is acquired with gradient echo-planar imaging (EPI) sequence of T2*-weighted images (TR/TE/flip angle: 3,000/35/90; FOV: 20*20 cml; matrix size: 64*64) divided to 44 axial slices (thickness: 3 mm; gap: 0 mm) covering the whole cerebrum. fMRI data preprocessing includes correction for head movement, realignment, normalizing the images to Montreal Neurological Institute (MNI) space, and spatially smoothing the data (FWHM: 6 mm). In addition, a set of harmonics is used to account for low-frequency noise in the data ($\frac{1}{128}$ Hz), and the first six images of each functional scan are rejected to allow for T2*equilibration effects. fMRI data analysis is done by SPM5 or Brain Voyager 1.10 following General linear model or data driven approach. The continuous EEG data is recorded simultaneously with fMRI acquisition throughout the experimental sessions. EEG is collected using an MR-compatible system including a 32-channel BrainCap electrode cap with sintered Ag/AgCl ring electrodes (30 EEG channels, 1 ECG channel, and 1 EOG channel; Falk Minow Services, Herrsching-Breitbrunn, Germany), and BrainAmp-MR EEG amplifier (Brain Products, Munich, Germany). Raw EEG is sampled at 5 kHz and recorded using Brain Vision Recorder software (Brain Products). EEG analyses are with EEGLAB 6.01 software package (Schwartz Center for Computational Neuroscience, University of California, San Diego), MATLAB software and FMRIB plug-in for EEGLAB. Pre-processing of the EEG data consists of MR gradient artifacts removal using a FASTR algorithm and Cardio-ballistic artifacts removal.

An optimized rt-fMRI (real-time fMRI) system includes state-of-the-art acquisition and analysis methods aimed at improving the accuracy of rt-fMRI signal measurement for learned regulation of brain activation. In fMRI, accurate signal measurement is compromised by low SNR, motion, and EPI artifacts. These concerns are more acute for rt-fMRI because analyses must be performed continuously on small increments of data (as opposed to an average over an entire experiment) and must be computed rapidly. rt-fMRI analysis is improved by online artifact rejection in the GLM and a newly developed method for estimating rt neural activations in a single volume. The following processing will take place online:

Artifact Detection and Rejection—Detecting and accounting for time-series artifacts during self-regulation experiments is significant to avoid providing the subject with inaccurate feedback. Ideally, volume to volume changes in fMRI data intensity would only be observed in the presence of changing neural activity. Subject motion is a prominent source of artifact in fMRI time series that can substantially degrade signal quality. Even small head motion can cause artifacts in activation estimates, particularly when the motion is correlated with the experimental paradigm 73 74. The rt-fMRI activation analysis is based on a novel GLM-based rt analysis method that is based on a single volume estimation.

In some embodiments, the signature comprises a regularized logistic classifier enabling to select and optimize regularization parameters improving spatial/temporal features for a given stimulus. As described above, the regularization parameters may be selected from a position of a least one pair of relevant electrodes on the subject's scalp; and for each pair of electrodes, relevant frequency bands in the EEG spectral data for a specific external stimulus; a frequency of the neural signal after the application of the stimulus, a maximal amplitude of the neural signal after the application of the stimulus, and at least one time point indicative of the best predicted mental state of the brain at which a change in frequency and/or in maximal amplitude is detected after the application of the stimulus.

In a specific and non-limiting example, the determination of the signature in step 110 is performed via machine learning-based model interpretation, which includes two models: (i) a localization model in which localization of relevant electrodes and time points is provided; and (ii) a frequency identification model in which inference of most relevant frequency bands for a specific stimulus is provided. The optimization of the model comprises determining a set of EEG measurement locations from which a part of the EEG data is measured corresponding to one or more regions responding to the stimulus by neural activity and determining time points of measurements corresponding to the response to the stimulus. The validation of the signature in step 112 is performed by: (iii) using the EEG limbic modulation index to monitor limbic activity modulation; and (iv) performing beam forming analysis to the EEG data.

The localization of relevant electrodes and time points may be based on a machine-learning-based method able to distinguish between brain states using EEG data from single trials. The brain functional state's category is defined according to the level of the activation in the fMRI images. This task is complicated by the different time-frequency resolution of EEG and fMRI.

The localization of relevant electrodes and time points may be performed using any suitable known technique. The following are two specific but not limiting examples of such techniques:

I. A logistic regression classifier is trained to predict the state of the subject. This technique describes the relationship between response variables Y to some explanatory variables X. The response variable has only two possible outcomes: event, denoted by 1 and non-event, denoted by 0.

The logit (log odds) of the logistic regressions' model is given by $$g(x) = w_0 + w_1 x_1 + w_2 x_2 + \ldots + w_p x_p \qquad (\text{eq. 1})$$

where $w_0, w_1, \ldots w_p$ are the parameters of the model.

The odd of an event is defined as the ratio of the probability that an event occurs to the probability that it fails to occur:

$$P(Y = 1 \mid x) = \pi(x) = \frac{e^{g(x)}}{1 + e^{g(x)}} = \frac{1}{1 + \exp(-yw^T x)} \qquad (\text{eq. 2})$$

$$\text{odds}(Y = 1) = \frac{P(Y = 1)}{P(Y = 0)} = \frac{\pi(x)}{1 - \pi(x)} = e^{g(x)} \qquad (\text{eq. 3})$$

An alternative form to write the model is as the function of the logit transformation:

$$\log \text{odds} = \log\left(\frac{\pi(x)}{1-\pi(x)}\right) = g(x) \quad \text{(eq. 4)}$$

Estimation of the coefficients $w=(w_0, w_1, \ldots, w_p)$ is often done using Maximum Likelihood Estimation (MLE), which seeks to maximize the log likelihood over the entire observed data:

$$l(w) = \sum_{i=1}^{n} \log P(Y = y_i \mid x_i) \quad \text{(eq. 5)}$$
$$= -\sum_{i=1}^{n} \log(1 + \exp(-y_i w^T x_i))$$

For proper estimation and comparison between models of different complexity, an additional regularization (penalty) function is used. A Matlab-based MVPA toolbox may be used to implement regularized logistic regression. The regularized version of the logistic regression algorithm seeks to find w which maximizes the equation:

$$l^\lambda(w) = l(w) - \frac{\lambda}{2} w^T w \quad \text{(eq. 6)}$$

The regularization also comes to solve a potential ill-posed problem due to a small amount of training data, and preventing over fitting. The accuracy of the classifier will be tested using m-k-fold cross validation. The original data is partitioned into k disjoint sets, where a single dataset is retained for test, and the remaining k−1 disjoint datasets are used for training the model. The cross-validation process is then repeated k times, with each of the k sets used exactly once as the test data. The whole process is repeated m times. In each training stage, the data is randomly split into n training and validation sets. For each such split, the training set to find the best model was used and its optimal regularization parameter $\lambda$ (within the range of interest), which bring the prediction error to minimum. The predictive accuracy of the model is assessed using the validation set. The results are then averaged over the splits.

After a model is chosen from a family of models, an error of the model is calculated using the test set as the number of wrongly predicted samples divided by overall number of samples.

This technique was applied on EEG signal using fMRI labels acquired simultaneously. A healthy subject was presented with pictures of faces in either the right or the left visual fields. The fMRI labels were taken from the right visual cortex then a threshold was applied on it. The 50% higher labels were considered as left faces (1) and the other were considered right faces (0). A set of N trials labeled data samples was obtained, each trial was represented by $N_{ch}$-by-$N_{tps}$ signal matrix, where $N_{ch}$ is the number of channels and $N_{tps}$ is the number of time sampling points in the segmented interval. The outcome of the classifier was compared for different time points and the time point which best predicted the mental state of the brain (i.e. left or right face) was selected.

II. A ridge regression classifier is trained to predict the state of the subject. This technique also describes the relationship between response variables Y to some explanatory variables X.

Ridge regression is appropriate for a linear relationship and it seeks w which minimizes the following expression:

$$\|y - Xw\|^2 \quad \text{(eq. 7)}$$

Regularized ridge regression adds a regularization term $\lambda$ to eq. 7 to determine the bias/variance trade-off.

$$\|y - Xw\|^2 + \lambda \|w\|^2 \quad \text{(eq. 8)}$$

A family of models is constructed, with different combinations of electrodes, frequency bands, time delays and model constraints. Then, a smaller collection of optimal models is selected using classical robust statistics methods for model selection and validation. These include cross validation and regularization at several levels of the feature extraction.

Two model evaluation strategies are applied:

The first uses normalized mean squared error (NMSE) to measure the similarity between the target signal and the predictor. If the NMSE is less than 1, then the prediction is doing better than the series mean.

$$NMSE = \frac{MSE(x)}{VAR(x)} = \frac{\sum_{i=1}^{n}(x_i - y_i)^2}{\sum_{i=1}^{n}(x_i - \bar{x})^2} \quad \text{(eq. 9)}$$

The second evaluation strategy uses Pearson's correlation to measure similar behavior instead of similarity.

$$\rho_{x,y} = \text{corr}(X, Y) = \frac{E[(X - \bar{X})(Y - \bar{Y})]}{\sigma_x \sigma_y} \quad \text{(eq. 10)}$$

This technique was applied by the inventors to predict the amygdale activity from EEG measurements. The activity of the amygdale was altered by requesting subjects to become relaxed. They received a sound feedback indicating their relaxation state as measured by their theta/alpha activity.

It is generally believed according to previous studies published that relaxation causes a decrease in the Alpha waves and an increase in the Theta waves. As a result the Theta-Alpha ratio should increase as the person relaxes.

Since the EEG and the fMRI have different resolutions and shift in time due to the hemodynamic response, usually the EEG is convolved with the canonical HRF function and down-sampled to the fMRI resolution.

Following preprocessing, which removes artifacts that are acquired during data acquisition, the higher temporal resolution data was down-sampled, while the lower temporal resolution data was up-sampled. The EEG data was then transformed into a detailed time-frequency representation using the Stockwell transformation.

The inventors demonstrated that a time-frequency representation of EEG data can predict the amygdale activity better than the traditional theta/alpha measurement that is convolved with the canonical HRF.

Figure 2A:
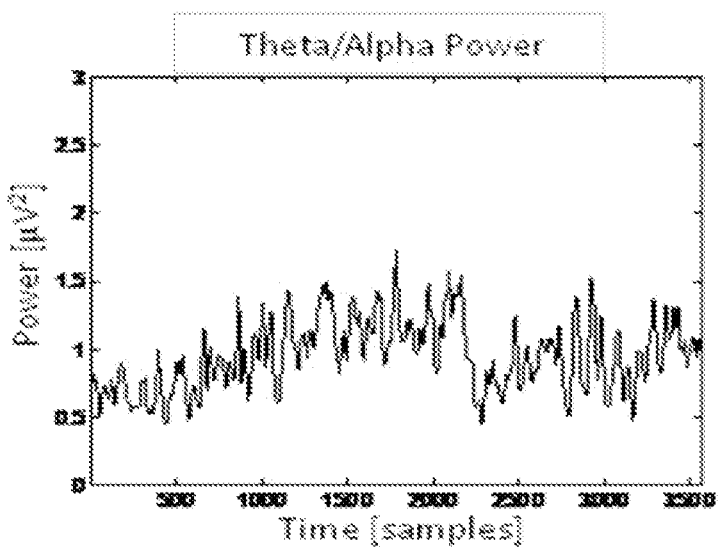
FIGS. 2A-2F illustrate results of an experiment performed by the inventors.

The results are shown in FIGS. 2A-2F. FIG. 2A shows the theta-alpha ratio variability. In the figure, Y-axis corresponds to the EEG power in $\mu V^2$, and X-axis corresponds to the time in samples, each sample being of 0.25 seconds. To get this ratio, the time-frequency EEG data was convolved with the canonical HRF and down-sampled to 4 Hz. The theta range taken was [4:7 Hz] and the alpha range taken was [8:13 Hz]. The frequency bands were averaged over three selected electrodes which achieved the highest ratio (i.e. averaged theta power over averaged alpha power). As can be seen, FIG. 2A depicts an increase in Theta/Alpha EEG power ratio.

Figure 2B:
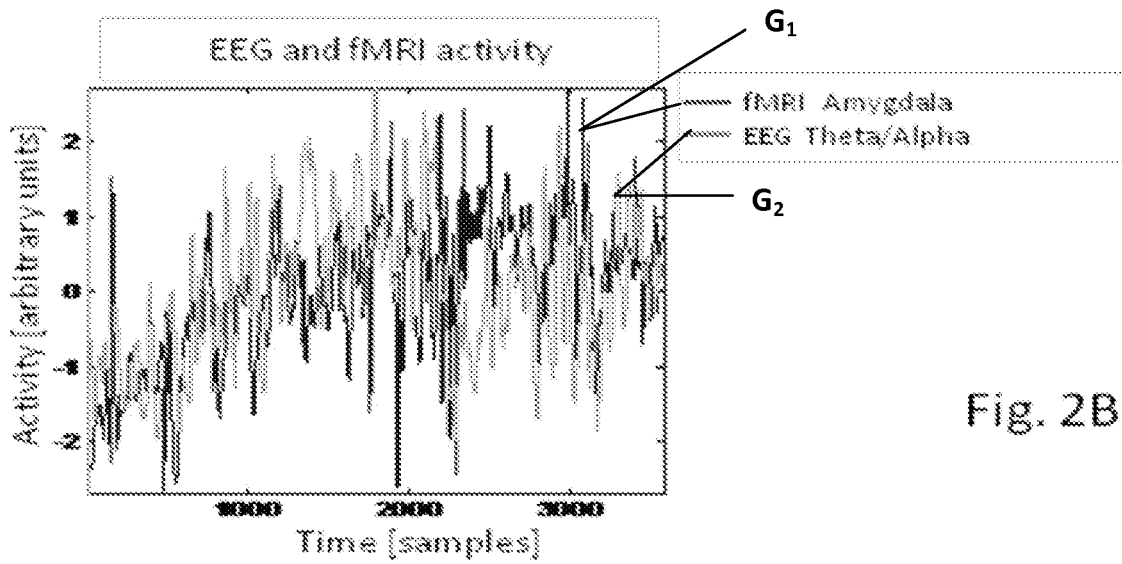

FIG. 2B shows the fMRI signal taken from the right amygdale (graph $G_1$), compared to the Theta/Alpha EEG signal (graph $G_2$). Both signals were normalized to arbitrary units for the purpose of demonstration. The fMRI signal was up-sampled also to 4 Hz. As said above, the inventors used EEG to predict the Amygdale signal seen in the fMRI. Activity which can be seen in the fMRI signal in time T, can be predicted using the intensity of frequency F of electrode C in delay D from T. This figure shows a high correspondence between the fMRI signal and the EEG signal, indicating that the task of increasing alpha/theta ratio as performed by the subject activated the amygdala as seen by fMRI.

Figure 2C:
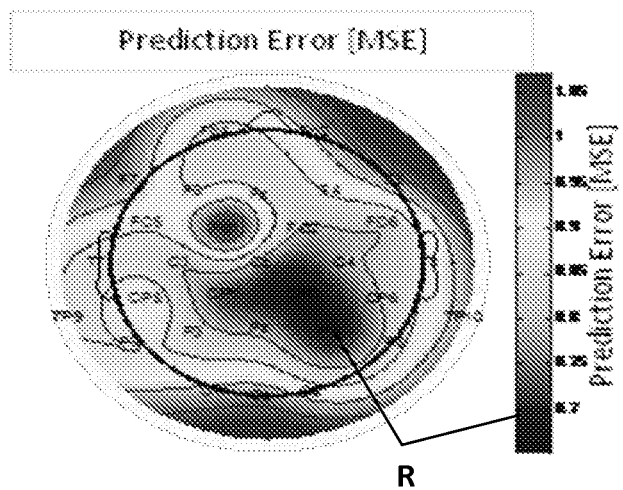

FIG. 2C shows the prediction results in different electrodes. EEG was recorded using a 32 electrode array. The prediction model was fitted to each electrode separately, yielding a prediction error for each electrode, measured in terms of NMSE (normalized mean squared error), the values in the lower region R of the ruler indicate good prediction strength. This map may indicate the activated areas during the relaxation process. As it can be seen, Electrode CP2 achieved the lowest error across validation sets. From this it may be concluded that this electrode contains much of the relevant information needed to make a good prediction of the relevant fMRI signal.

Figure 2D:
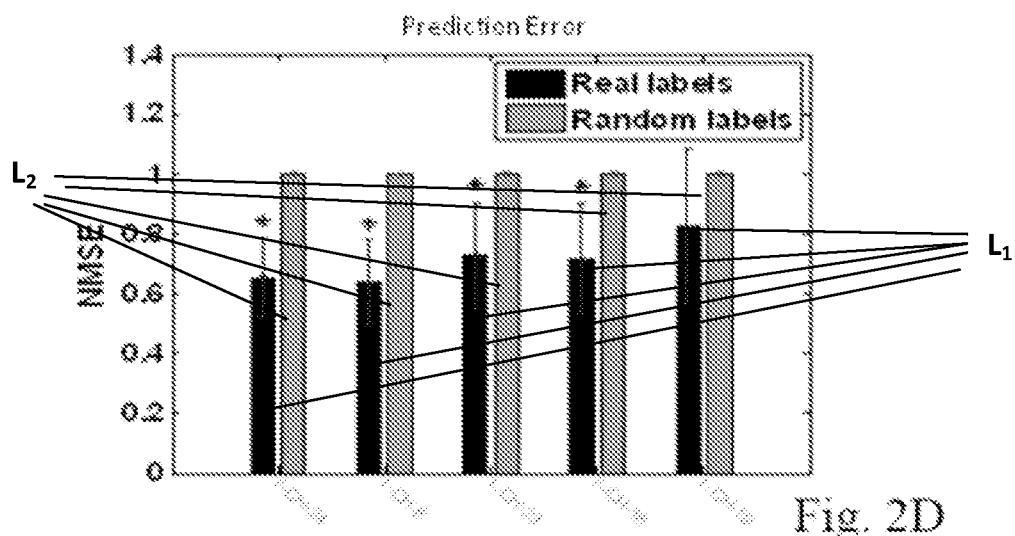

FIG. 2D shows prediction results (NMSE) on test sets (real labels $L_1$) for best 5 electrodes found on the validation sets. The results were compared to results using the same algorithm on randomly scrambled labels $L_2$, i.e. the target function for prediction was a randomly scrambled version of the true fMRI signal. This figure demonstrates that prediction error with random data is maximal, indicating that the classifier is not biased and does not over-fit the data. The results suggest that a ridge regression model which is based on time/frequency representation of EEG can predict the amygdale activity significantly better than chance.

Figure 2E:
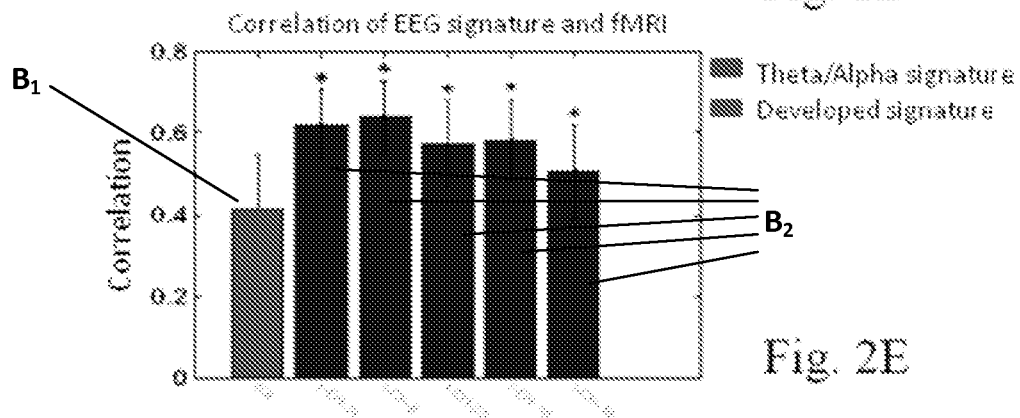

FIG. 2E shows prediction results (correlation) of the predictor found using ridge regression compared to the standard Theta/Alpha predictor (bar $B_1$) (on test sets). It can be seen that the prediction results were improved related to Theta/Alpha. Specifically, the graph shows the correlation coefficient between the signature as derived from various EEG electrodes (bars $B_2$) using a ridge regression model and the fMRI activity, and correlation between theta/alpha power and fMRI activity (bar $B_1$). This graph suggests that the derived signature has higher correlation to the fMRI data than the standard theta/alpha signature.

Figure 2F:
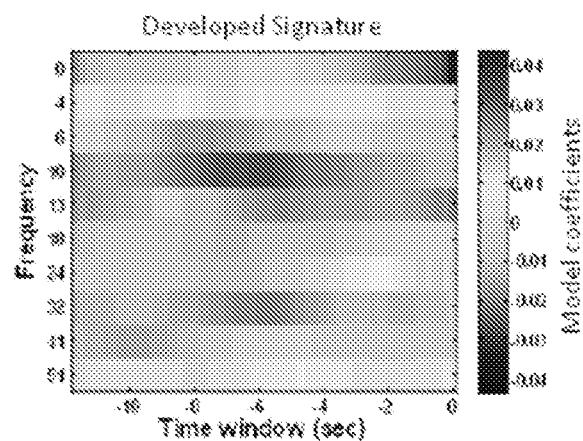

FIG. 2F shows ridge coefficients for each frequency band and shift of the best electrode (the one that achieved the minimal NMSE on the validation sets). This map may indicate relevant frequencies and specific time delays of the activity which constitute a model for a signature. Specifically, each value in the matrix plot represents a value of the weight (coefficient) vector w from eq. 8. Each row of the matrix plot represents a frequency band used in the time-frequency representation (X from eq. 8) of the data. Each column in the matrix plot represents a specific time shift of the time-frequency representation of the data. This figure can be considered as an example of graphical representation of the derived model for the EEG signature of the amygdala fMRI.

The results showed that the obtained prediction is significantly better than chance and prediction improvement that can be achieved with the traditional theta/alpha measurement. In addition, map of the prediction results in different electrodes may indicate the activated areas during the relaxation process and ridge coefficients for the best electrode may indicate relevant frequencies and specific time delay of the activity.

This experiment demonstrated that it is possible to improve the spatial resolution of EEG and consequently, to improve the temporal resolution of concurrent EEG/fMRI. The spatial resolution improvement does not require many electrodes, and may be adapted to individual subjects.

The frequency identification model determining the inference of most relevant frequency bands for a certain brain condition (e.g. in response to a specific stimulus) may be performed as follows:

The EEG temporal data is first processed by, for example, applying a Fourier transform to provide an EEG spectral data. The frequency identification model includes the development of a regularized logistic regression classifier to identify frequencies in the EEG spectral data in which most of the EEG signal's variance occurs during a given stimulus. This classifier determines the linear combination of frequencies, which contribute most to the EEG signal during each of the states, according to eq. (1), where x is a matrix of time frequency transform of the signal from one EEG electrode.

The frequency identification model parameters are the weights of the frequency contribution to the prediction. The response variables (i.e. the predicted labels) are the fMRI activity of one or more regions. The relevant electrode for this regression is selected according to the electrode coefficients resulting from the localization model described above. Preliminary results have shown unique features in the EEG frequencies to a stimulus being in the present example an experimental task of eyes open or close under light and dark conditions.

In an experiment performed by the inventors, 10 subjects performed a simple eyes opening and closing task in blocks of 30 sec for 3 minutes, designed to trigger alpha waves in the EEG (Berger effect). This experiment was performed under room light and dark conditions. Time-frequency decomposition of the EEG signal from one electrode, calculated by using Stockwell transform was used as input to the classifier. A logistic regression classifier was trained to predict the state of the subject (opened or closed eyes) and its optimal frequency features where estimated by using cross validation. Performance of the classifier was estimated again with cross validation procedure.

In this example, the frequency identification model includes the classifier's performance at each electrode serving as a spatial localizer of information relevant to the stimulus/task. Frequency weights of the prediction under light conditions show a large contribution of the alpha band (8-14 Hz) to the prediction, as expected from the Berger Effect, but additional frequencies other than alpha contribute significantly to the prediction. Frequency weights of prediction under darkness condition show contribution of the alpha band to the prediction. The location of electrodes with lowest prediction error was proved to be different from the one under light conditions, and it was mostly frontal. This diverse localization and distribution of frequencies may suggest two distinct brain mechanisms operating under the different light conditions.

The validation of the signature may be performed by using the EEG limbic modulation index to monitor limbic activity modulation as follows:

The localization and frequency of model's parameters, which have been obtained with the techniques described above, may be used to determine the functional brain level in real time, from an EEG recording and return a feedback to the subject. Specifically, a combination of electrodes determined by the localization model is used as an input to the frequency identification model. This frequency identification model is trained to predict limbic system activity. The output of this model is a model of frequency weights, and these weights are applied to EEG frequencies estimated in real time during the NF experiment. This can give an EEG index of limbic activity (signature) in real time, and may be used for feedback to the subject during the NF. The inventors have demonstrated a set of numerical models, which enable a robust model interpretation (brain state) from single trials, finding relevant EEG electrodes, temporal location and spectral band of the response, enabling to obtain an accurate (individually based) brain functional index of a subject.

The validation of the signature may be performed by performing beamforming analysis of the EEG data as follows:

The source estimation is done by the Fieldtrip software package. This approach is best applied in the frequency domain, but time domain applications also exist. Coherence information and connectivity data are readily available for any EEG time series that is statistically stationary (ongoing and with a stable covariance matrix over time). Generally, these analyses are clearly superior—both in terms of reliability and spatial specificity, to other more commonly used methods.

Figure 3:
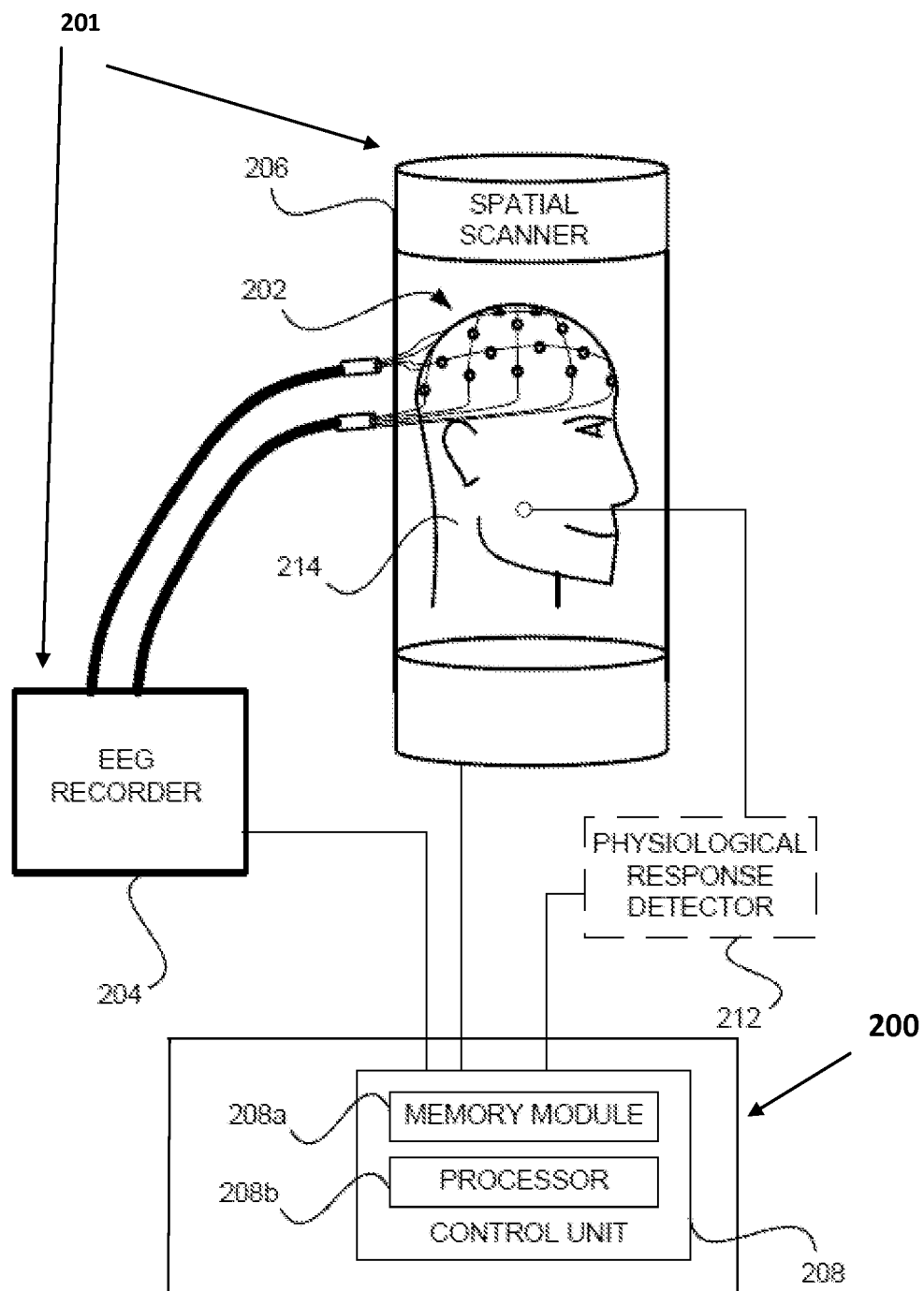
FIG. 3 is a schematic drawing illustrating a possible configuration of the system of the present invention for use in the determination of the signature in the EEG data.

Reference is made to FIG. 3 showing schematically a system 200 of the invention for use in monitoring a subject's brain activity to determine the brain activity signature.

The system 200 includes a control unit 208 which is typically a computer system utilizing inter alia a memory module 208a and a processor utility 208b, and also including data input and output utilities (not shown). The control unit 208 is connectable (via wires or wireless signal transmission) to a measured data collecting device 201, which may be a measurement device itself or a separate storage device. In the present not limiting example, the measured data collecting device 201 is constituted by the measurement device, which in this example includes an EEG electrodes' arrangement 202 in communication with an EEG recording device 204, and a spatial scanner 206.

It should be noted that the control unit of the present invention provides a novel configuration. Such control unit may be a stand-alone device or may be mounted with any system of any type if needed including the configuration of the present invention.

In some embodiments, the control unit 208 is configured and operable for creating a database for use in analyzing brain activity of a subject. The control unit 208 comprises a data input utility (not shown) and a processor utility. The data input utility is configured for receiving measured data comprising data corresponding to signals indicative of a subject's brain activity originated from multiple measurement locations during a certain time period. The processor utility is preprogrammed for processing the measured data and generating data indicative thereof in the form of a multi-parameter function presenting a relation between frequency and time data of the measured signals and the multiple measurement locations. The processor utility is further adapted for analyzing this relation and identifying a subject-related signature corresponding to the subject's brain neural activity, where the signature is in the form of a frequency and time function over selected set of locations from the multiple measurement locations.

In the specific but not limiting example, the measured comprises EEG data (first measured data) and spatial scan data (second measured data) simultaneously measured on brain of a specific subject. The data processor utility 208b is configured for processing the measured data, determining a relation between the EEG data and the spatial scan data, and determining one or more EEG signatures indicative of a certain spatial neural activation as corresponding to one or more regions in the subject brain, thereby enabling use of the one or more signatures for further interpretation of a brain functional state of subjects by using EEG data.

Optionally the system 200 further includes a physiological measurement device 212. The control unit 208 is also configured to control and optionally synchronize an operation of each of the above elements of the system 200. As indicated above, the control unit 208 may also include a memory unit 208a for storing data.

The EEG electrodes' arrangement 202 is configured and operable for being disposed on the scalp of a subject 214, detect electrical signals emitted by neural activity of the subject's brain, and convey the measured signals to the EEG recording device, where the signals are stored, and processed into EEG data. Generally the processing includes matching the signal amplitude with the time of detection, in order to obtain a waveform of the signal amplitude as a function of time. The EEG data is sent to the control unit 208.

The spatial scanner 206 is configured and operable to generate at least one image of the subject's brain, where regions of neural activity are differentiated from regions where no neural activity is present. Spatial scanners suitable for this may include fMRI scanners, MEG scanners, HEG scanner, PET scanners, CT imaging devices, SPECT imaging devices, or imaging devices based on ultrasound tagging of light, for example. Images generated by the spatial scanner 206 are also sent simultaneously to the control unit 208.

The control unit 208 is configured and operable for receiving EEG data from the EEG recorder 204, and an image indicative of the region or network of neural activity of the subject's brain from the spatial scanner 206. All the received information is processed by the processor 208b of the control unit 208 in order to analyze the EEG data and find therein a signature that corresponds to the active neural region/network of the subject's brain. The processing may be performed in real time, i.e. shortly after the information has been received, or the information may be stored in the memory module 208a, for later processing.

Optionally, a physiological measurement device 212 is present for detecting a physiological response associated with a change of neural activity at a specific region or network in the subject's brain. The physiological measurement device 212 is used as an additional tool, in order to verify neural activity in a region or network of the subject's brain or to improve the identification of the EEG signature. The detector 212 may include, for example, an electrocardiography (ECG) device designed for measuring the heartbeat of the subject 214, and/or a skin conductance measurement device designed for measuring moisture in the subject's skin (and therefore the production of sweat by the subject 214). The measurements taken by the detector 212 are sent to the control unit 208.

An output interface may be used in order to apply a stimulus to the subject 214. The output interface may include a screen for displaying text, an image, or a movie to the subject 214. Optionally or alternatively, the output interface may include a speaker or earphones for conveying a sound to the subject 214. The subject's reaction to the stimulus is recorded in the EEG recorder 204, the spatial scanner 206, and the physiological measurement device 212, if present. It should be noted that a stimulus may be applied to the subject 214 in other manners, which do not necessitate the output interface. These manners may include, for example, asking the subject to solve a complex or unsolvable mathematical/logical problem within a given time. As explained above, in reference to FIG. 1B, the stimulus is aimed at triggering neural activity in a predetermined region/network of the subject's brain.

In some embodiments of the present invention, the system 200 is programmed to apply different stimuli at different times, according to a predetermined procedure (as mentioned above, in reference to FIG. 1B). This enables a generation and analysis of data corresponding to the activation of different regions/networks in the subject's brain, and therefore enables an increase in the amount of data generated within a session with the subject 214. In these embodiments, the output interface may be controlled by the control unit 208 to convey to the subject 214 different stimuli at different times, according to the procedure.

Figure 4:
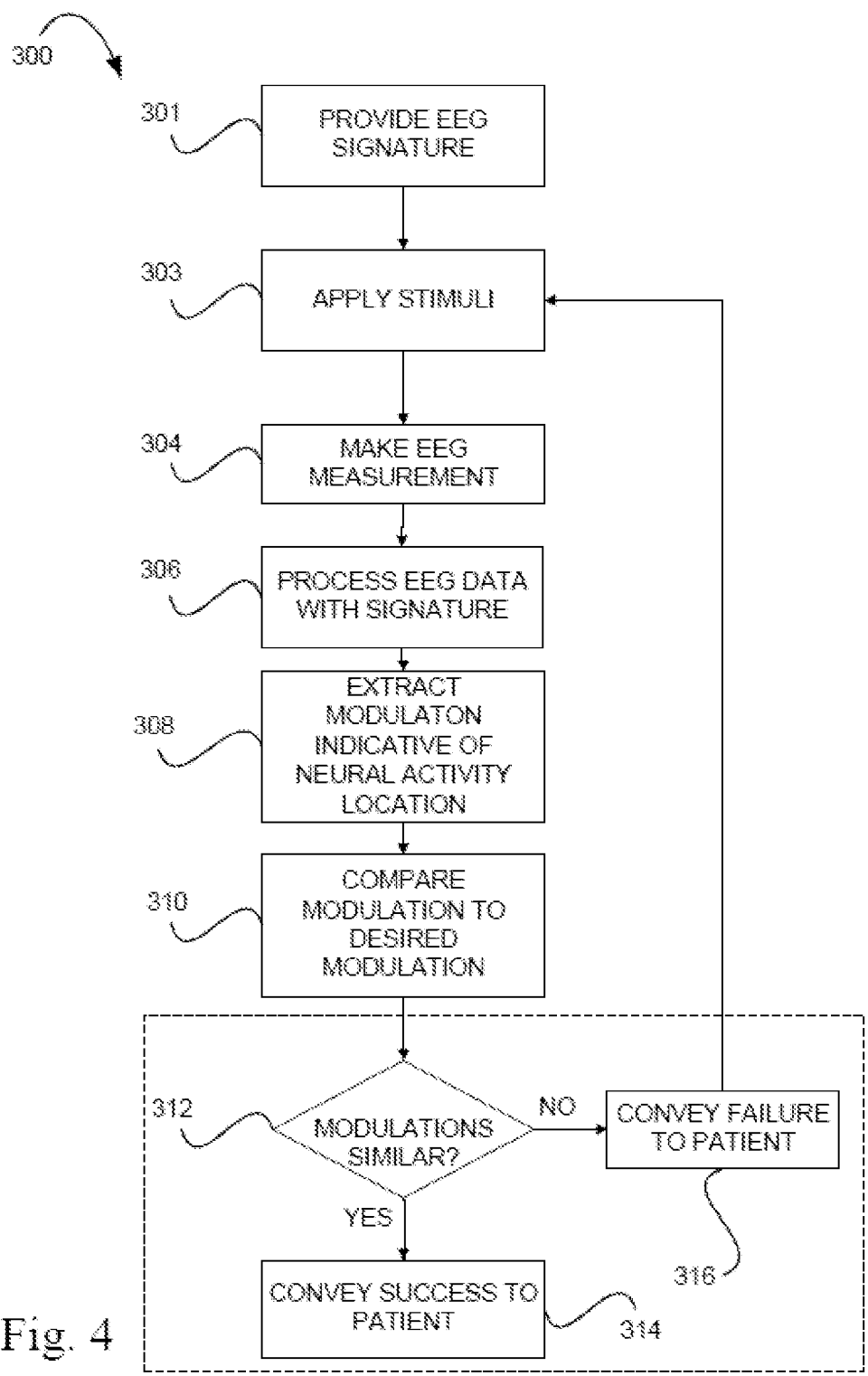
FIG. 4 is a flowchart illustrating an example of a method of the present invention used in a NF session.

FIG. 4 is a flowchart exemplifying a method 300 for use in performing an exercise of a NF session, in which a region of neural activity is indicated by a signature extracted from EEG data. Feedback of a change in the activity of the region is given to the subject in real time. The method 300 comprises providing a predetermined EEG signature corresponding to a certain stimulus at 301; applying the stimulus to a subject to activate the one or more brain regions at 303; performing an EEG measurement on the subject's brain at 304 while under the application of the certain stimulus, and generating EEG data thereof; processing the EEG data using the predetermined EEG signature at 306 to identify one or more parameters indicative of neural activation of the one or more regions by the given stimulus, and selecting from the EEG data EEG signals related to the neural activation.

To identify the EEG signature, the above described method and system (FIGS. 1A-1B and 3) may be used. The signature identification/creation method may thus be a preliminary session performed for each subject before step 303, for the purpose of determining one or more signatures. In another variant, in the event that the signatures are common to a plurality of subjects, the comparison relies on a database of signatures previously extracted from a plurality of subjects. As described above, the predetermined EEG signature is indicative of a spatial neural activation of one or more regions in a subject's brain corresponding to individual functions of the brain while under the certain stimulus and thus corresponds to a predicted certain activity state related to a given stimulus.

At 304, an EEG measurement of the subject's neural activity is taken via an EEG electrodes' arrangement, and may be recorded in an EEG recorder. The EEG measurement is made continuously starting before the instruction to the subject and ending at a predetermined time after the instruction has been made, in order to detect a change (if any) in the neural signals brought about by the subject's attempt at modulation, and in order to collect enough EEG data for enabling a processing thereof.

At 308, a modulation of limbic activity indicative of the region or network in the brain at which neural activity is present is extracted from the processed EEG signals. At 310, the modulation extracted at 308 is compared to a desired modulation of the subject's brain corresponding to the predicted certain activity state. The desired modulation may correspond, for example, to a relaxed state of the subject. At 312, a degree of correlation between the modulation of limbic activity and the desired modulation of limbic activity is then obtained to enable to determine a psychological evaluation of the subject. If the degree of correlation is high, such as, but not limited to, significant person correlation coefficient, then a success message is conveyed to the subject at 314. If the degree of correlation is low such as insignificant person correlation coefficient, then a failure message is conveyed to the subject at 316, and optionally, the stimulus is applied again on the subject at 303. The success and failure messages may be conveyed to the subject via an image, a video, or an audio signal.

As mentioned above, the signature in the EEG data corresponds not only to a region or network of activity in the subject's brain, but also to a stimulus causing such an activity. In some embodiments of the present invention, it is possible to identify a cognitive state of the subject's brain corresponding to either a desired or an undesired functional state. In such an event, NF may be used to help the subject to either strengthen a desirable self-applied impulse, or to weaken an undesirable self-applied impulse, in order to reach a desired modulation of the subject's brain.

Optionally, an internal check subprocess is included in method 300. Simultaneously with the EEG measurement, a physiological property of the subject is also measured, to verify a change of neural activity at predetermined regions or networks in the subject's brain. As mentioned above, the physiological property may include, for example the subject's heartbeat (measured, for example, via ECG), and/or the subject's sweat production (detected, for example, via a measurement of the subject's skin conductivity).

Optionally, the region(s) or network(s) of neural activity in the subject's brain is identified, by referring to the map created via the above-described method of signature creation. A predetermined physiological property corresponding to neural activity in the identified region is compared to the physiological property measured, in order to ensure that the method 300 is working as planned. If the measured physiological property behaves according to a correct physiological response (i.e. the physiological response known to occur for a state of activity/inactivity of the identified region/network), the method 300 is being properly applied. If the measured physiological property does not behave according to the correct physiological response for the identified region/network, chances are that the method 300 is not being properly applied, and the method is interrupted, in order to find out why. Such physiological measurements can therefore be used as additional data and parameters that may be used for the improvement of the prediction of the state of activity of identified region.

Figure 5:
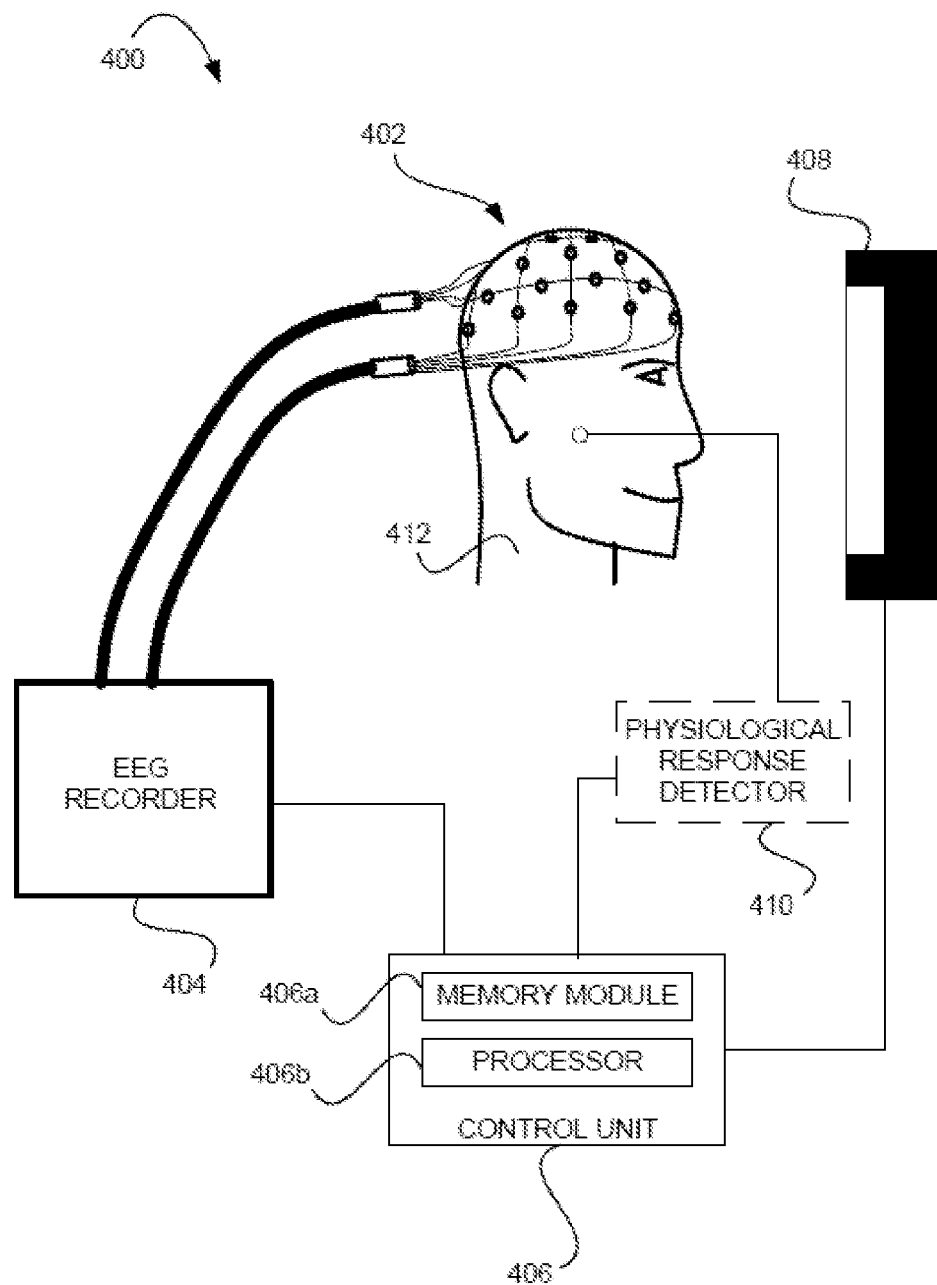
FIG. 5 is a schematic drawing illustrating an EEG-based system of the present invention for performing a NF session.

FIG. 5 is a schematic drawing illustrating an EEG-based system 400 for use in performing a NF session. The system 400 may be configured for being used after a signature has been determined, according to the above-described method of FIGS. 1A and 1B and/or via the system 200 of FIG. 3.

The system 400 includes an EEG measurement unit 402, a control unit 406 comprising a memory utility 406a for storing data and data processor 406b for processing data. The EEG measurement unit 402 is configured for placing on a scalp of a subject and for detecting electrical signals originated by neural activity of a subject's brain, and generating EEG data thereof. To this end, the EEG measurement unit 402 is associated with an EEG recorder 404. The memory utility 406a is configured for storage of a predetermined EEG signature indicative of spatial neural activation of one or more regions in a subject brain corresponding to individual functions of the brain. As indicated above, the EEG signature corresponds to a predicted response of subject's brain activity to at least one certain stimulus. The data processor 406b is configured and operable for receiving the EEG data and for processing the EEG data utilizing stored data about the predetermined EEG signature to identify one or more parameters corresponding to neural activation of one or more region for a given stimulus applied to a specific subject during the EEG measurements. The control unit 406 controls and optionally synchronizes an operation of each of the above elements of the system 400, according to predetermined commands. Such commands may be fixed, or the control unit 406 may be programmable, so that the commands are changeable by a user, according to the user's need.

In some embodiments, the system 400 comprises an output interface 408 configured for conveying a feedback message to a subject in real time indicating success or failure of the subject to provide a desired response to a given stimulus, according to a signal generated by the control unit such that the subject is trained to regulate the neural activity of the region via the feedback message. The subject 412 is asked to achieve a desired modulation of the subject's brain. The EEG data is sent to the control unit 406. The EEG measurement may be made continuously starting before the instruction to the subject and ending at a predetermined time after the instruction has been made to the subject 412, as explained before, with reference to step 304 of FIG. 4. In one variant, the beginning and end of the measurement period are selected by a user (e.g. medical personnel) via an input interface (such as a keyboard or a button, or a voice activated device). In another variant, the instruction is given to the subject 412 via the output interface 408, and the control unit 406 controls the timing of the EEG measurement period, as well as the timing of the instruction within the EEG measurement period. Optionally, the control unit 406 is programmable by a user, enabling the user to determine the EEG measurement period and the timing of the instructions to the subject 412.

Optionally, the system 400 comprises a physiological property detector 410 for detecting a physiological response (i.e., property change) associated with a change of neural activity at a specific region or network in the subject's brain. Measurements effected by the physiological property detector 410 are also sent to the control unit 406.

In some embodiments of the present invention, the control unit 406 is configured and operable for performing the internal check subprocess. In such embodiments, the map constructed via the method 100 (relating EEG signatures to neural activity in regions/networks in the brain) and a map relating physiological reactions to neural activity in regions/networks in the brain is stored in the memory module of the control unit 406.

The system 400 is able to indicate the region or network in the subject's brain in which neural activity is found, via an analysis of the EEG data. The system 400, therefore, includes the benefits of spatial scanners (fMRI, MEG scanners, for example) without a need thereof. The lack of expensive and bulky spatial scanners enables the system 400 to be smaller in size than the current NF systems, and therefore to be located in small clinics or even be portable for use on the field. The system 400 provides a novel EEG-based clinical tool being portable, easy to use and low cost. NF sessions are therefore no longer limited to hospitals or research centers. Furthermore, because of the lack of high magnetic fields typically generated by spatial scanners, a need for removing and/or reducing induction artifacts from EEG measurements is reduced. The system 400 is based on (portable) EEG only, and has both diagnostic and therapeutic capabilities. The system 400 may be used for early diagnosis of vulnerability to psychopathology as well as for individually-tailored intervention and prevention protocols aimed at improving brain cognitive regulation abilities. The system 400 used with NF procedures targeted at deep brain areas and guided by the neural activation index generated by the control unit 406 improves the individual's ability to regulate specific brain functions.

The invention claimed is:

1. A method for identifying a brain activation signature, the method comprising:
    providing a first set of spatial fMRI scan data corresponding to and showing activation of at least one brain region during an indicated time period and a second set of EEG temporal data measured by an EEG measurement unit at different measurement locations on a scalp during said indicated time period;
    analyzing said second set of EEG temporal data by selecting a specific set of measurement locations and measurement time points in said time period, and by identifying relevant frequency bands and/or relevant signal amplitudes and/or relevant signal amplitudes power in said temporal data;
    identifying a correlation between the results of said analyzing and said activation of said at least one brain region as measured in said fMRI scan data to generate a brain activation signature of said second set of EEG temporal data which includes an indication of said at least one brain region and corresponds with activation of said at least one brain region, wherein said brain activation signature is in a form of a function describing a subset selection of frequency, time data and measurement locations which is sufficient for indicating activation of said at least one brain region without additional spatial scan data; and
    storing said brain activation signature in a memory.

2. The method of claim 1, wherein the stored brain activation signature comprises one or more brain activation signatures, and data indicative of one or more brain states corresponding to the signatures.

3. The method of claim 1, comprising applying certain one or more stimuli to the subject such that the measured data corresponds to the subject's brain response to said one or more stimuli.

4. The method of claim 1, comprising repeating said providing, said analyzing, said identifying and said storing on a plurality of subjects and creating a database of signatures that is stored in the memory.

5. The method of claim 1, further comprising: developing a feedback protocol for training a specific subject for a certain stimulus, by identifying a modulation of at least one parameter of the signature, while under the application of the certain stimulus, corresponding to a functional state of the subject's brain at which one or more regions from which the measure signals are originated are at a desired activity level, and using the identified signature to select temporal signals indicative of said functional state.

6. The method of claim 5, comprising:
    providing a predetermined EEG signature corresponding to a certain stimulus, said predetermined EEG signature being indicative of a spatial neural activation of one or more regions in a subject brain corresponding to individual functions of the brain while under said certain stimulus and thus corresponding to a predicted certain activity state related to a given stimulus;

applying said stimulus to a subject to activate said one or more brain regions; and performing EEG measurements on the subject's brain for a controlled time period while under the application of the certain stimulus, and generating EEG data thereof; processing said EEG data using said predetermined EEG signature to identify one or more parameters indicative of neural activation of said one or more regions by said given stimulus, and selecting from the EEG data EEG signals related to said neural activation.

7. The method of claim 6, comprising: extracting a modulation of limbic activity from the EEG signals, comparing the extracted modulation of limbic activity to a desired modulation of limbic activity corresponding to said predicted certain activity state; and determining a degree of correlation between the modulation of limbic activity and the desired modulation of limbic activity, enabling to determine a psychological evaluation of said subject.

8. The method of claim 6, comprising: upon identifying that the extracted modulation and the desired modulation have a high degree of correlation, conveying a message indicating success to the subject; and upon identifying that the extracted modulation and the desired modulation have a low degree of correlation, conveying a message indicating failure to the subject, such that the subject is trained to monitor limbic activity modulation of said one or more regions.

9. The method of claim 8, further comprising, after conveying a message indicating failure to the subject, repeating the EEG measurement on the subject while under the application of said stimulus and processing the EEG data.

10. The method of claim 1, further comprising:
collecting a new set of temporal data; and
analyzing said new set of temporal data using said stored brain activation signature to identify activation of said at least one brain region.

11. The method of claim 1, wherein said signature comprises a signature of activation of the amygdala.

12. The method of claim 1, wherein identifying a correlation comprises generating a per-person signature.

13. The method of claim 1, wherein identifying a correlation comprises generating a signature across people.

14. The method of claim 1, wherein identifying a correlation comprises generating a signature for a brain network.

15. A method for validating a brain activation signature, the method comprising:
(a) providing a first set of fMRI spatial scan data corresponding to and showing activation of at least one brain region during an indicated time period and a second set of EEG temporal data measured by electrodes of an EEG measurement unit during said indicated time period;
(b) analyzing said second set of EEG temporal data by selecting a specific set of electrodes and measurement time points in said time period and by identifying relevant frequency bands used in the measurement of said temporal data;
(c) identifying a correlation between the results of said analyzing and said activation of at least one brain region as measured in said fMRI scan data, to generate a first EEG brain activation signature including an indication of said at least one brain region and corresponds to the subject's brain neural activity of said at least one selected brain region, wherein said brain activation signature is in a form of a function describing a subset selection of frequency, time data and measurement locations which is sufficient for indicating activation of said at least one brain region without additional spatial scan data;
(d) storing said first EEG brain activation signature in a memory; and
(e) validating said first EEG brain activating signature by,
(i) activating said at least one brain region;
(ii) measuring a set of EEG temporal data during said activating;
(iii) repeating (b)-(c) to generate a second EEG brain activation signature;
(iv) comparing said second EEG brain activation signature to said first EEG brain activation signature; and
(v) determining that said first EEG brain activation signature is valid, if said first EEG brain activation signature is similar to said second EEG brain activation signature.

16. The method of claim 15, further comprising:
collecting a new set of temporal data; and
analyzing said new set of temporal data using said stored first brain activation signature to identify activation of said at least one brain region.

17. A system for use in monitoring brain activity of a subject, comprising:
a computer system having a processor and a non-transitory computer readable memory connected to the processor;
a data input utility, wherein said data input utility executable by said processor is configured to receive a first set of EEG data corresponding to high temporal resolution signals measured by an EEG measurement unit during an indicated time period, and a second set of fMRI scan data corresponding to and showing activation of at least one brain region thereof;
wherein said processor is configured to generate a multi-parameter function presenting a relation between said high temporal resolution EEG data of said first set of data and said second set of fMRI scan data, to generate a brain activity signature from said first set of EEG data, which includes an indication of said at least one brain region and correlates with activation of said at least one brain region based on said multi-parameter function, wherein said brain activation signature is in a form of a function describing a subset selection of frequency, time data and measurement locations which is sufficient for indicating activation of said at least one brain region without additional spatial scan data, and to store said brain activity signature in said memory.

18. The system of claim 17, wherein said stored brain activity signature is used to identify activation of said at least one brain region.

19. The system of claim 17, wherein said data input utility is connectable to a first measurement unit and/or to a second measurement unit.

20. The system of claim 19, wherein the first measurement unit comprises electrodes and the measured data comprises electrical data measured on multiple electrodes configured to be placed at the multiple locations of a subject's scalp.

21. The system of claim 20, wherein the electrical data is electroencephalography (EEG) data.

22. The system of claim 20, wherein the first measurement unit comprises electrodes, the second measurement unit comprises an imaging device, and the first measured data comprises electrical data measured by said electrodes configured to be placed at one or more locations of the subject's scalp, and the second measured data being image data taken by the second measurement unit indicative of spatial scan of the multiple locations in the subject's brain; wherein the processor is configured and operable to use said image data for improving spatial resolution of the first measured data and to generate said signature.

23. The system of claim 17, wherein said data input utility is connectable to at least one of the following: an output of said memory where said measured data is stored; and an output said measured data collecting device for collecting said measured data.

24. The system of claim 17, wherein said processor is configured and operable to identify said brain activity signature by optimization of a value of one or more parameters of at least one predetermined model stored in the memory; said parameters being selected from at least one of: providing a set of measurement locations from which a part of said first type data is measured; determining time points of measurements of said signals; processing the first and second type data to determine spectral data and a relation between one or more frequency bands in the spectral data with the measurement location data to obtain inference of the frequency bands related to neural activation of one or more regions in the brain.

25. The system of claim 17, further comprising a noninvasive physiological measuring device, for independently measuring at least one physiological property of the subject being of a kind changing in response to neural activity in one or more regions of the brain;
said processor being further configured and operable to receive the measured physiological response via said data input utility and ensure that the brain activity signature identified indicates neural activity at the corresponding region, via a comparison of the measured physiological response to a previously determined physiological response associated with neural activity of the corresponding region.

26. The system of claim 17, wherein said processor is configured and operable to create a database of brain activity signatures and store said database in the memory, the brain activity signatures being classified according to at least one of the following: subject's population, and brain states.

27. The system of claim 17, wherein said data input utility is connected to at least one measured data collecting device.

28. The system of claim 27, wherein said data input utility is connected to said at least one measured data collecting device for collecting measured data, wherein the measured data collecting device comprises:
a first measurement unit comprising an EEG electrodes arrangement configured to be placed on a scalp of the subject and to detect said signals as electrical signals originated by neural activity of the subject's brain, said EEG electrodes configured and operable to generate the first set of data including EEG data indicative thereof;
the a second measurement unit comprising a spatial scanner configured and operable to scan the subject's brain and identify one or more regions of neural activity in the subject's brain and an activity level of said one or more regions corresponding to individual functions of the brain, and to generate the second set of scan data as spatial scan data;
wherein said processor is configured and operable to control simultaneous operation of the EEG electrodes arrangement and the spatial scanner, and to receive and analyze the EEG data and the spatial scan data, to generate an EEG signature indicative of a spatial neural activation of one or more regions in the subject brain, thereby enabling use of said signature for further interpretation of at least one brain region activation state of said subject by using the EEG data.

29. The system of claim 27, wherein said at least one measured data collecting device comprises a first and a second measurement unit, and the control unit is configured and operable to control simultaneous operation of the first and second measurement units and to receive and analyze the first and second type data to identify the signature indicative of a spatial neural activation of one or more regions in the subject brain, thereby enabling use of said signature for further interpretation of a brain functional state of said subject by using measured data provided by the first measurement unit.

30. The system of claim 28, wherein the spatial scanner comprises at least one of: a magnetic resonance imaging (MRI) scanner; a functional magnetic resonance imaging (fMRI) scanner; a magneto encephalographic (MEG) scanner; hemoencephalography (HEG) scanner; magnetic resonance spectroscopic imaging (MRS); positron emission tomography (PET); X-ray computed tomography (CT) imaging device; single photon emission computed tomography (SPECT) imaging device; and a scanner based on ultrasound tagging of light or photoacoustic imaging.

31. A system for use in monitoring brain activity of a subject using EEG enhanced using additional data, the system comprising a control unit comprising:
a data input utility for receiving measured data comprising data corresponding to signals measured during a certain time period and being indicative of a subject's brain activity and originated from the subject's brain during said certain time period, wherein said measured data is temporal and spatial data comprising first electroencephalography (EEG) temporal data being time and frequency function of EEG signals measured by an EEG measurement unit, and second spatial functional magnetic resonance imaging (fMRI) data for multiple locations within the brain provided by a fMRI scanner; and
a processor utility which is configured and operable for (a) analyzing said EEG temporal data by selecting a specific set of measurement locations and measurement time points in said time period; (b) identifying one or more parameters to be used in the processing of said measured EEG temporal data, wherein said parameters comprise one or more of frequency bands, signal amplitudes and signal amplitudes power; (c) processing the measured data using said identified one or more parameters and generating data indicative thereof in the form of a multi-parameter function presenting a relation between frequency and time data of said first EEG temporal data measured by the EEG measurement unit and said second spatial fMRI data measured from the multiple locations within the brain by said fMRI scanner; (d) analyzing said relation and identifying based on said analyzed relation at least one selected brain region; and for (e) generating a subject-related EEG signature based on said analyzed relation, including an indication of said at least one selected brain region and -corresponding to the subject's brain neural activity of said at least one selected brain region, wherein said subject-related EEG signature is in a form of a function describing a subset selection of frequency, time data and measurement locations which is sufficient for indicating activation of said at least one brain region without additional spatial scan data.

32. The system of claim 31, wherein said EEG measurement unit is configured to measure said first EEG temporal data corresponding to high temporal resolution signals during an indicated time period.

33. The system of claim 32, wherein said EEG measurement unit comprises at least one EEG electrode placed on a scalp of said subject configured to measure said first EEG temporal data.

34. The system of claim 31, wherein said second spatial fMRI data comprises scan data corresponding to and showing activation of said at least one brain region thereof.

35. The system of claim 34, wherein said control unit comprises a non-transitory computer readable memory connected to the processor for storing said subject-related EEG signature.

36. The system of claim 35, wherein said stored subject-related EEG signature is used to identify activation of said at least one brain region.

37. The system of claim 31, wherein said processor utility is configured to process said first EEG temporal data by selecting a specific set of measurement locations and measurement time points in said time period, and by identifying relevant frequency bands and/or relevant signal amplitudes and/or relevant signal amplitudes power in said EEG temporal data.

38. The system of claim 31, wherein said processor utility is configured and operable for said identifying one or more frequency bands from frequency bands in a range of 0-51 Hz including frequency bands different from frequencies of alpha waves.

39. The system of claim 31, wherein said at least one selected brain region comprises limbic regions.

40. The system of claim 31, wherein said at least one selected brain region comprises the amygdala.

41. The system of claim 31 wherein said subject-related signature is used for interpretation of a brain functional state of said at least one selected brain region of said subject from EEG temporal data recorded from the brain of said subject, and for providing a feedback signal to said subject based on said interpretation.

42. The system of claim 41, wherein said at least one selected brain region comprises the amygdala and wherein said subject is a subject diagnosed with PTSD.

43. The system of claim 31, wherein said EEG measurement unit is configured to measure said temporal data, and/or said spatial scanner is configured to measure said spatial data while said subject reacts to a specific stimulus selected to trigger neural activity in said at least one selected brain region.

44. The system of claim 31, wherein said multi-parameter function presents a relation between frequency of said measured EEG signals and time data of said neural activity of at least one selected brain region measured in said spatial fMRI data, within a time delay window of up to 12 seconds.

45. The system of claim 31, wherein said processor utility is configured and operable for analyzing a new set of EEG data using said generated EEG signature and said new EEG data to identify activation of said at least one selected brain region without processing new spatial scan data.

46. The system of claim 45, wherein said processor utility is configured and operable during said analyzing to identify using said generated EEG signature a portion in said new EEG data that correlates with activation of said at least one selected brain region.

47. A method for processing EEG signals using fMRI signals to generate and EEG signature, the method comprising:

providing a first set of spatial functional magnetic resonance imaging (fMRI) scan data measured by a fMRI scanner and corresponding to and showing activation of one or more brain regions during an indicated time period and a second set of EEG temporal data measured by an EEG measurement unit at different measurement locations on a scalp during said indicated time period;

analyzing said second set of EEG temporal data by selecting a specific set of measurement locations and measurement time points in said time period;

selecting one or more parameters to be used in the processing of said EEG temporal data, wherein said parameters comprise one or more of frequency bands, signal amplitudes and signal amplitudes power;

processing said EEG temporal data using said selected one or more parameters to generate a multi-parameter function presenting a relation between frequency and time data of said EEG temporal data measured at said different locations on said scalp;

identifying a correlation by a computer system between the results of said processing and said fMRI scan data indicating activation of least one selected brain region of said one or more brain regions; and generating a brain activation signature which includes an indication of said at least one selected brain region and corresponds to the subject's brain neural activity of said at least one selected brain region, wherein said brain activation signature is in a form of a function describing a subset selection of frequency, time data and measurement locations which is sufficient for indicating activation of said at least one selected brain region without additional spatial scan data.

48. The method of claim 47, further comprising:
collecting a new set of EEG temporal data; and
analyzing said new set of EEG temporal data using said generated brain activation signature and said EEG temporal data to identify activation of said at least one selected brain region without processing new spatial scan data.

49. The method of claim 48, wherein said multi-parameter function presents a relation between frequency of said measured EEG signals and time data of said neural activity of at least one selected brain region measured in said spatial fMRI data, within a time delay window of up to 12 seconds.

50. The method of claim 48, comprising:
delivering a feedback signal related to the identified activation of said at least one brain region.

51. The method of claim 50, wherein said delivering comprises delivering said feedback signal to a PTSD patient.

52. The method according to claim 48, wherein said at least one brain region comprises the amygdala.

53. The method of claim 48, wherein said analyzing comprises identifying using said generated brain activation signature a portion in said new set of EEG data that correlates with activation of said at least one selected brain region.

54. The method of claim 47, wherein said selecting comprises selecting said one or more frequency bands from frequency bands in a range of 0-51 Hz including frequency bands different from frequencies of alpha waves.

55. The method of claim 47, wherein said first set of spatial fMRI data and said second set of EEG temporal data are measured in a healthy subject.

* * * * *